US008992834B2

(12) United States Patent
Nomura et al.

(10) Patent No.: US 8,992,834 B2
(45) Date of Patent: Mar. 31, 2015

(54) BLOOD GLUCOSE LEVEL MEASURING APPARATUS AND METHOD, AND MEASUREMENT DATA MANAGEMENT APPARATUS

(75) Inventors: Takafumi Nomura, Kanagawa (JP); Kou Ishikawa, Kanagawa (JP); Masayoshi Suda, Kanagawa (JP); Toshihisa Nakamura, Kanagawa (JP); Hideyuki Momoki, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1004 days.

(21) Appl. No.: 13/076,099

(22) Filed: Mar. 30, 2011

(65) Prior Publication Data

US 2011/0196218 A1    Aug. 11, 2011

Related U.S. Application Data

(63) Continuation of application No. PCT/JP2009/066564, filed on Sep. 24, 2009.

(30) Foreign Application Priority Data

Sep. 30, 2008  (JP) ................. 2008-254830

(51) Int. Cl.
*G01N 33/00*  (2006.01)
*C12Q 1/00*  (2006.01)
(Continued)

(52) U.S. Cl.
CPC .............. *C12Q 1/006* (2013.01); *A61B 5/1411* (2013.01); *A61B 5/14532* (2013.01);
(Continued)

(58) Field of Classification Search
CPC ............... A61B 5/14532; C12Q 1/006; G01N 33/48792; G01N 35/00871
USPC .......................................... 422/68.1, 500, 67
See application file for complete search history.

(56) References Cited

U.S. PATENT DOCUMENTS

| | | |
|---|---|---|
| 2004/0117062 A1 | 6/2004 | Bonney et al. |
| 2004/0172284 A1 | 9/2004 | Sullivan et al. |
| 2010/0256990 A1 | 10/2010 | Horiguchi et al. |

FOREIGN PATENT DOCUMENTS

| | | |
|---|---|---|
| EP | 1837787 A1 | 9/2007 |
| EP | 1956508 A2 | 8/2008 |

(Continued)

OTHER PUBLICATIONS

Extended European Search Report issued on Jul. 3, 2013, by the European Patent Office in corresponding European Patent Application No. 09817685.2 (6 pages).

(Continued)

*Primary Examiner* — Sam P Siefke
(74) *Attorney, Agent, or Firm* — Buchanan Ingesoll & Rooney PC

(57) ABSTRACT

A blood glucose level measuring apparatus and measurement data management apparatus are provided which can carry out measurement of the blood glucose level of a plurality of patients relatively rapidly and reliably, while also addressing emergency situations. The blood glucose level measuring apparatus includes a patient identifier, blood glucose level measuring device, a date/time counter, a display, and a controller. The controller controls in a normal measurement mode the cross-checking of patient identification information and a patient data table, and then, if patient identification information is not found, measurement of the blood glucose level is inhibited. The controller also controls in an emergency measurement mode in which carrying out of measurement of the blood glucose level is permitted without acquiring the patient identification information by the patient identifier.

12 Claims, 13 Drawing Sheets

(51) Int. Cl.
*A61B 5/15* (2006.01)
*A61B 5/145* (2006.01)
*A61B 5/157* (2006.01)
*G06F 19/00* (2011.01)
*G01N 33/487* (2006.01)
*G01N 35/00* (2006.01)

(52) U.S. Cl.
CPC ........... *A61B 5/157* (2013.01); *G06F 19/3406* (2013.01); *G06F 19/3418* (2013.01); *G01N 33/48792* (2013.01); *A61B 2560/0242* (2013.01); *A61B 2562/08* (2013.01); *G01N 35/00871* (2013.01); *G01N 2035/00881* (2013.01)
USPC ............................................ 422/67; 422/68.1

(56) References Cited

FOREIGN PATENT DOCUMENTS

| | | |
|---|---|---|
| JP | 2-279056 A | 11/1990 |
| JP | 10-019888 A | 1/1998 |
| JP | 10-318928 A | 12/1998 |
| JP | 2000-060803 A | 2/2000 |
| JP | 2003-099529 A | 4/2003 |
| JP | 2003-215122 A | 7/2003 |
| JP | 2003-337861 A | 11/2003 |
| WO | WO 02/078593 A2 | 10/2002 |
| WO | WO 2009/031636 A1 | 3/2009 |

OTHER PUBLICATIONS

International Search Report (PCT/ISA/210) issued on Oct. 27, 2009, by Japanese Patent Office as the International Searching Authority for International Application No. PCT/JP2009/066564 and an English translation of the International Search Report.

BLOOD GLUCOSE LEVEL MEASURING APPARATUS AND METHOD, AND MEASUREMENT DATA MANAGEMENT APPARATUS

This application is a continuation of International Application No. PCT/JP2009/066564 filed on Sep. 24, 2009, and claims priority to Japanese Application No. 2008-254830 filed on Sep. 30, 2008, the entire content of both of which is incorporated herein by reference.

TECHNICAL FIELD

This invention generally relates to a technique suitable for application to a blood glucose level measuring apparatus and a measurement data management apparatus. More particularly, the present invention pertains to a blood glucose level measuring apparatus and a measurement data management apparatus which can execute measurement of the blood glucose level and dosage of insulin to a plurality of patients in a hospital safely and with relative certainty and can rapidly deal also with an emergency.

BACKGROUND DISCUSSION

As well known in the art, diabetes arises from abnormal secretion of insulin of the pancreas. Therefore, it is necessary for a diabetic to measure the blood glucose level before a meal and dose insulin in response to the blood glucose level.

Conventionally, in order to allow a patient or a family of the patient in a home to measure the blood glucose level simply and conveniently, the assignee of the present invention has developed and manufactures and sells a blood glucose level measuring apparatus (hereinafter referred to as "blood glucose meter"). Examples of blood glucose meters are described in Japanese Patent Laid-Open No. Hei 10-19888 and Japanese Patent Laid-Open No. Hei 10-318928

In a hospital caring for a large number of patients, a safety countermeasure is required to prevent mix-up of patients, overlapping dosage of insulin and so forth. Further, it is necessary to collectively carry out a blood glucose level measuring process and an insulin dosage process for many patients while taking the medical working efficiency into consideration.

Now, a new blood glucose meter is desired which is refined in function from the point of view of safety, operational efficiency and so forth and is intended for a medical site or facility. In order to prevent a medical mishap, it is investigated to confirm, in the case where a blood glucose meter is used in a hospital, personal identification information to confirm a nurse who should carry out blood glucose level measurement and confirm each patient to measure the blood glucose level of the patient.

However, an apparatus which cannot carry out measurement if identification information of a user such as a nurse or identification information of a patient is not inputted to the apparatus upon sudden change of the condition of a patient, upon a natural calamity such as earthquake or in a like situation is not well suited to coping quickly with the situation.

SUMMARY

A blood glucose level measuring apparatus comprises: identification means for acquiring patient identification information identifying a patient, blood glucose level measuring means for measuring blood glucose level of the patient; date/time counting means for obtaining date/time information identifying the date and time at which the blood glucose level is obtained by the blood glucose level measuring means; a display configured to display the patient identification information of the patient acquired by the identification means, the blood glucose level of the patient measured by the blood glucose level measuring means, and the date and time information obtained by the date/time counting means indicating the date and time at which the blood glucose level is obtained; a patient data table configured to store the patient identification information; and control means for effecting control. During a normal measurement mode the control means crosschecks the patient identification information acquired by the identification means and the patient data table, and, if the patient identification information is found in the patient data table, permit measurement of the blood glucose level by the blood glucose level measuring means, but if the patient identification information is not found in the patient data table, prevents measurement of the blood glucose level. In an emergency measurement mode, the control means permits measurement of the blood glucose level without acquiring the patient identification information by the identification means. A changing means allows changing of the measurement mode from the normal measurement mode to the emergency measurement mode. The apparatus also includes a measurement data table in which, after the blood glucose level is obtained in the normal measurement mode, the blood glucose level and the date/time information identifying the date and time at which the blood glucose level is obtained are recorded in an associated relationship with the patient identification information but, in the emergency measurement mode, the blood glucose level and the date/time information are recorded in an associated relationship with mode information indicating the emergency measurement mode, under the control of the control means The blood glucose level measuring apparatus permits quite rapid and reliable normal measurement to be carried out, and also makes it possible to immediately cope with an emergency.

The blood glucose level measuring apparatus can also include notification means for issuing, where the present mode is the emergency measurement mode, a notification that the present mode is the emergency measurement mode or is not the normal measurement mode.

This thus helps avoid a situation in which the current mode for measurement is mistaken.

The apparatus can also include communication means for determining, regarding one of blood glucose levels recorded in the measurement data table, the patient identification information, blood glucose level, information of date/time at which the blood glucose level is obtained and mode information as one string of transmission data wherein a non-recorded item is determined as blank information and transmitting the transmission data regarding all of the blood glucose levels recorded in the measurement data table to an external apparatus. This allows the management of data to be carried out by a measurement data management apparatus when emergency measurement is performed.

The control means can be outfitted with a history mode in which, in the normal measurement mode, the blood glucose level and the information of date/time, at which the blood glucose level is obtained, which are associated with the selected patient identification information are displayed on the display means, but in the emergency measurement mode, the blood glucose level and the information of date/time, at which the blood glucose level is obtained, which include the mode information are displayed on the display means and, if the identification means acquires the patient identification information, then the blood glucose level and the information of date/time at which the blood glucose level is obtained are recorded into the measurement data table in an associated relationship with the patient identification information. When sufficient time is available after emergency measurement or in a like situation, a measured blood glucose level can be associated with patient identification information ex post facto, and it can be made most of readily in later data management, life guidance of a patient and so forth.

A measurement data management apparatus for managing data of the blood glucose level measuring apparatus further includes host communication means for communicating with the communication means, a patient history table adapted to record the blood glucose level and the information of date/time at which the blood glucose level is obtained in an associated with the patient identification information, a temporary patient measurement file adapted to record one string of transmission data wherein the patient identification information is blank information, and host control means for extracting the patient identification information from the one string of transmission data and cross-checking the extracted patient identification information and the patient history table with each other and then recording, if the patient identification information is found from within the patient history table, the blood glucose level and the information of date/time at which the blood glucose level is obtained into the patient history table in an associated relationship with the patient identification information but recording, if the patient identification information is not found from within the patient history table, the blood glucose level and the information of date/time into the temporary patient measurement file.

This measurement data management apparatus makes it relatively easy to manage data of a blood glucose level measured by the blood glucose level measuring apparatus.

According to another aspect, a blood glucose level measuring apparatus comprises: identification means for acquiring patient identification information identifying a patient whose blood glucose is to be measured; blood glucose meter comprising a reagent which interacts with a blood sample to provide a measurement of the blood glucose level of the patient; date/time counting means for obtaining date/time information identifying the date and time at which the patient's blood glucose level is measured by the blood glucose meter; a patient data table configured to store the patient identification information; a display on which is displayed the patient identification information of the patient acquired by the identification means, the blood glucose level of the patient measured by the blood glucose meter, and the date/time information obtained by the date/time counting means; changing means for changing a measurement mode during which the patient's blood glucose level is measured from a normal measurement mode to an emergency measurement mode; control means for: permitting the blood glucose meter to measure the blood glucose level of the patient during the emergency measurement mode without requiring the identification means to acquire patient identification information; for permitting the blood glucose meter to measure the blood glucose level of the patient during the normal measurement mode when the patient identification information is acquired by the identification means and matches patient identification information in the patient data table; and for preventing the blood glucose meter from measuring the blood glucose level of the patient during the normal measurement mode when the patient identification information is acquired by the identification means but does not match patient identification information in the patient data table; and a measurement data table to which is recorded in an associated relationship: the blood glucose level measured in the normal measurement mode together with the date/time information identifying the date and time at which the blood glucose level is measured in the normal measurement mode; and the blood glucose level measured in the emergency measurement mode together with the date/time information identifying the date and time at which the blood glucose level is measured in the emergency measurement mode and mode information indicating the emergency measurement mode.

Another aspect disclosed here involves a method of measuring blood glucose level in a patient in a normal measurement mode and in an emergency measurement mode. The method comprises: if the normal measurement mode is selected: acquiring patient identification information identifying a patient whose blood glucose level is to be measured; cross-checking the acquired patient identification information with a patient data table to determine if the patient identification information is in the patient data table; permitting measurement of the blood glucose level of the patient if the patient identification information is in the patient data table, identifying the blood glucose level of the patient and also identifying the date and time at which the blood glucose level of the patient is measured in the normal measurement mode; and preventing measurement of the blood glucose level if the patient identification information is not in the patient data table; changing from the normal measurement mode to the emergency measurement mode; identifying the blood glucose level of the patient measured in the emergency measurement mode, and also identifying the date and time at which the blood glucose level of the patient is measured in the emergency measurement mode, without acquiring the patient identification information identifying the patient whose blood glucose level is measured in the emergency measurement mode; displaying the measured blood glucose level of the patient, and the date and time at which the blood glucose level of the patient is measured; recording in an associated relationship in a measurement data table during the normal measurement mode: the blood glucose level, the date and time at which the blood glucose level is measured, and the patient identification information; and recording in an associated relationship in the measurement data table during the emergency measurement mode: the blood glucose level, the date and time at which the blood glucose level is measured, and emergency mode information identifying the emergency measurement mode.

According to the disclosure here, a novel blood glucose level measuring apparatus and method, and a novel measurement data management apparatus are provided which can carry out measurement of the blood glucose level of a plurality of patients rapidly and with certainty and can rapidly deal also with an emergency situation.

BRIEF DESCRIPTION OF THE DRAWING FIGURES

DETAILED DESCRIPTION

Figure 1:
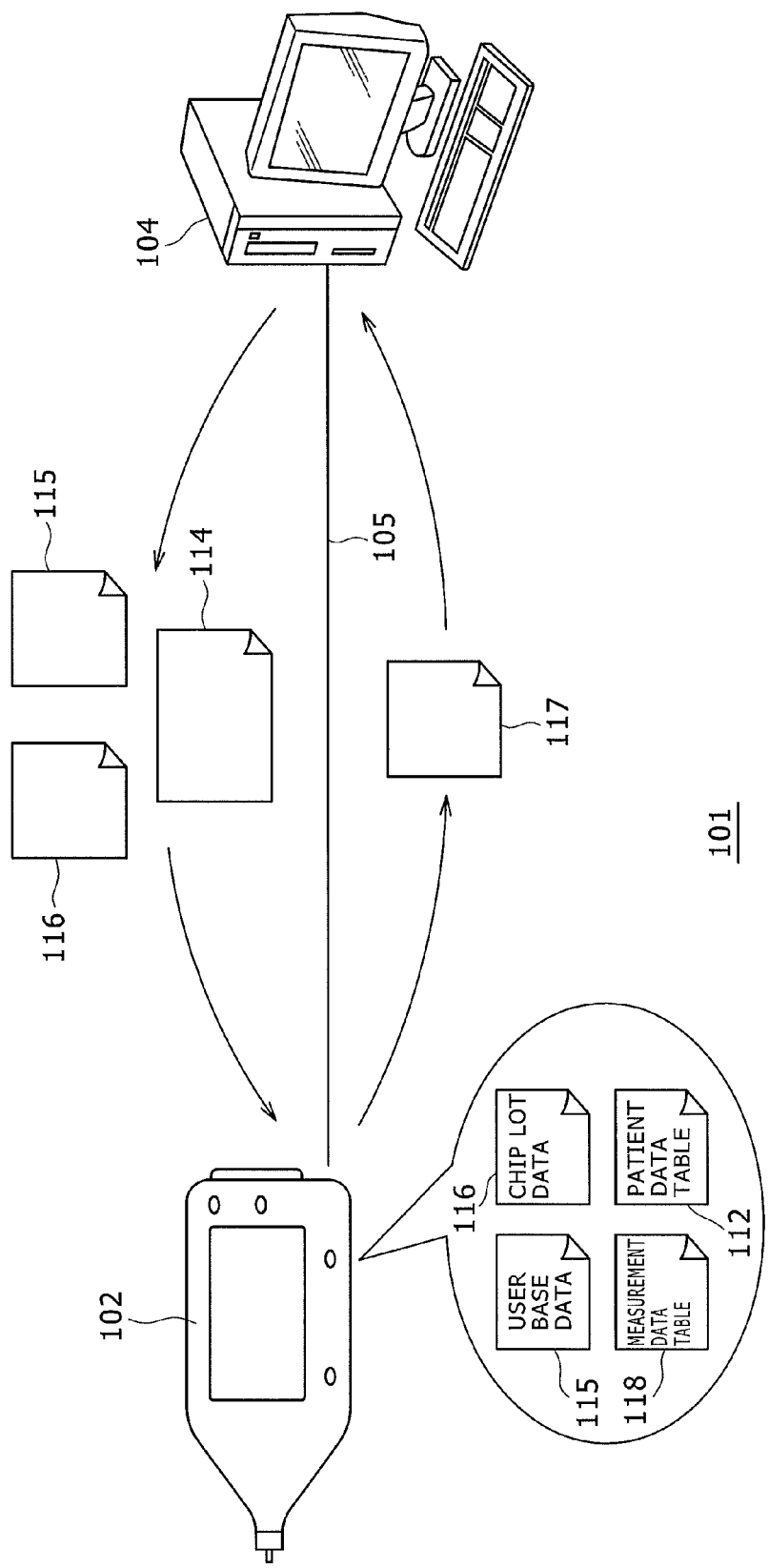
FIG. 1 is a general schematic view of an example of one embodiment of a blood glucose level measuring system.

Referring to FIG. 1, the blood glucose level measuring system 101 includes a blood glucose meter 102 (blood glucose level measuring apparatus or blood glucose level measuring means) and a measurement data management apparatus 104.

The blood glucose meter 102 is a portable apparatus which operates with a lithium ion battery and has a size with which it can be generally accommodated in a hand of an adult.

When a doctor, a nurse or the like is to measure the blood glucose level of a patient, usually the blood glucose meter 102 is brought into a ward in a medical facility (e.g., hospital), takes a very small amount of a blood sample from an earlobe, a finger, an arm or the like of the patient and measures the blood glucose level.

After the measurement of the blood glucose level, the blood glucose meter 102 can transmit and receive data to and from the measurement data management apparatus 104. The measurement data management apparatus 104 which is formed from a personal computer is connected to the blood glucose meter 102 by a USB cable 105.

A well-known OS (operating system) operates in the measurement data management apparatus 104. Further, on the OS, a program for allowing the personal computer to implement functions as the measurement data management apparatus 104 operates.

The blood glucose meter 102 is a measuring instrument for puncturing, for example, a finger of a subject to take a blood sample and measuring the blood glucose level, and a blood glucose level measuring element 202 measures the blood glucose level of the sample blood of the patient. The measuring method of the blood glucose level may be any of a method wherein a blood sample is taken and caused to react with a reagent to measure the blood glucose level and a noninvasive method wherein the blood glucose level is measured from body fluid. In order to take a blood sample (body fluid), a puncturing tool for exclusive use is prepared separately and is punctured into such a living organism surface as, for example, a fingertip, a brachial part, an abdominal part, a femoral region or an ear polyp.

The blood glucose meter 102 is connected to the measurement data management apparatus 104 through the USB cable 105 to execute communication with the measurement data management apparatus 104. Thereupon, if a measurement data table 118 exists in the blood glucose meter 102, then measurement data stored in the measurement data table 118 is transmitted to the measurement data management apparatus 104.

Further, if a predetermined command is transmitted from the measurement data management apparatus 104, then the measurement data management apparatus 104 can download blood glucose meter setting data from the blood glucose meter 102.

Furthermore, the measurement data management apparatus 104 can upload patient data 114, user base data 115 and tip lot data 116 to the blood glucose meter 102.

The communication between the blood glucose meter 102 and the outside is not limited to the communication described above, as a wire or wireless communication system can be used, and a measurement result and so forth stored in a storage unit of the blood glucose meter may be outputted to a server which manages the blood glucose level in a hospital, a health management supporting equipment or the like through an information communication network such as the Internet.

[Blood Glucose Meter 102]

Figure 2:
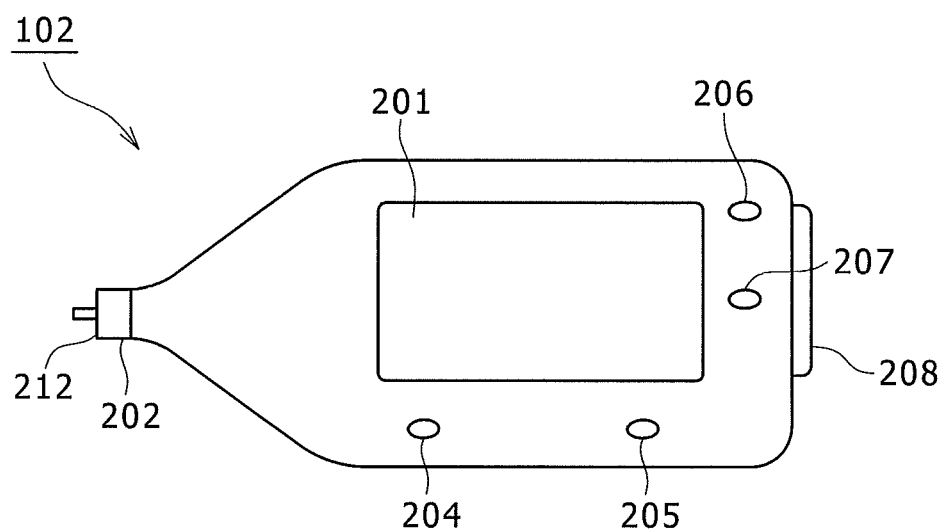
FIG. 2 is a plan view of a blood glucose meter.

Referring to FIG. 2, features of the blood glucose meter 102 are described. For convenience of description, the face on which a display (e.g., LCD) is provided as shown in FIG. 2 is referred to as the body surface, and the left side of FIG. 2 is referred to as the forward end direction while the right side is referred to as the rearward end direction.

As shown in FIG. 2, the blood glucose level measuring element 202 for measuring the blood glucose level using test paper which contains a color reagent which develops a unique color with glucose is provided at the forward end of the blood glucose meter 102. The blood glucose level measuring element 202 is shaped such that a blood glucose measuring tip 212 (hereinafter referred to as "measurement tip") is removably mounted thereon.

The blood glucose meter 102 has an operation portion and a display portion. The display portion of the meter includes a display that displays information. In this disclosed embodiment, the display is an LCD unit 203 having a liquid crystal display screen is provided on the body surface of the blood glucose meter 102. The operation portion includes a power supply button 204 and a start button 205 below the display 203. An emergency button 206 and a history button 207 are provided in the rearward end direction of the LCD unit 203. The LCD unit 203 is an example of a display means for displaying information such as the patient identification information of the patient, the blood glucose level of the patient and the date/time information at which the blood glucose level is obtained.

Furthermore, on a rear end side face of the blood glucose meter 102, a barcode reader 208 is provided as an example of identification means for identifying patient information. As the identification means described above, not only a barcode reader but also ten keys, an IC tip reader and so forth can be used. Further, at a position, a USB connection port is provided. A battery lid for allowing replacement of a battery and an infrared communication window are provided on the rear surface of the blood glucose meter 102.

The operation portion may be any element such as a pushbutton, ten keys or the like only if it operates the blood glucose meter. Further, the display portion is provided for displaying a measured blood glucose level, a message to an operator or the like, and a liquid crystal display apparatus is used preferably.

The power supply button 204 is a switch for switching the power supply to the blood glucose meter 102 between on and off.

The start button 205 is a button for selecting a normal mode in which patient identification information is confirmed to carry out blood glucose level measurement after the power supply button 204 is switched on. Further, in the case where a barcode is used as patient identification information, the start button 205 serves also as a barcode reader activation button for activating the barcode reader 208 in order to read in the barcode.

The emergency button 206 is a button for selecting an emergency mode in which blood glucose level measurement is carried out without confirmation of patient identification information after the power supply button 204 is switched on. The emergency button 206 is an example of a changing means for changing the measurement mode from the normal measurement mode to the emergency measurement mode.

The history button 207 is a button for displaying measurement data stored in a measurement data table of the blood glucose meter 102.

The barcode reader 208 is the barcode reading apparatus formed from a known combination of a red laser diode and a light receiving element. It is to be noted that it is also possible to use an image sensor such as a CCD image sensor or a CMOS image sensor.

The basic mechanism for blood glucose measurement of the blood glucose meter 102 is similar to that which is known in the art. A general description is set forth below.

The measurement tip 212 is attached to the blood glucose level measuring element 202, and the blood of a measurement object person is absorbed in the measurement tip 212. This measurement tip 212 has a built-in test paper formed from a porous membrane or the like of polyethersulfone or the like. Then, the blood absorbed in the measurement tip 212 reacts, when it arrives at the test paper, with the reagent contained in the test paper and develops color. Although the color development reaction requires a period of time from several seconds to approximately 10 and several seconds, this reaction is influenced by the surrounding air temperature.

After the predetermined reaction time elapses, light is irradiated upon the test paper from the light emitting element and reflected light from the test paper is received by the light receiving element. Then, an analog received light intensity signal obtained from the light receiving element is converted into a digital value, and the digital value is converted into the blood glucose level and displayed on the LCD unit 203.

The mechanism of the blood glucose meter 102 side is not limited to that of the optical measurement type which makes use of a coloring reagent, but a mechanism such as an electrochemical sensor type which can be used for blood glucose measurement heretofore can be adopted.

The blood glucose meter 102 is connected to the personal computer through the USB cable 105. Also it is possible to carry out the connection by infrared communication through the infrared communication window provided on the surface.

[Hardware]

Figure 3:
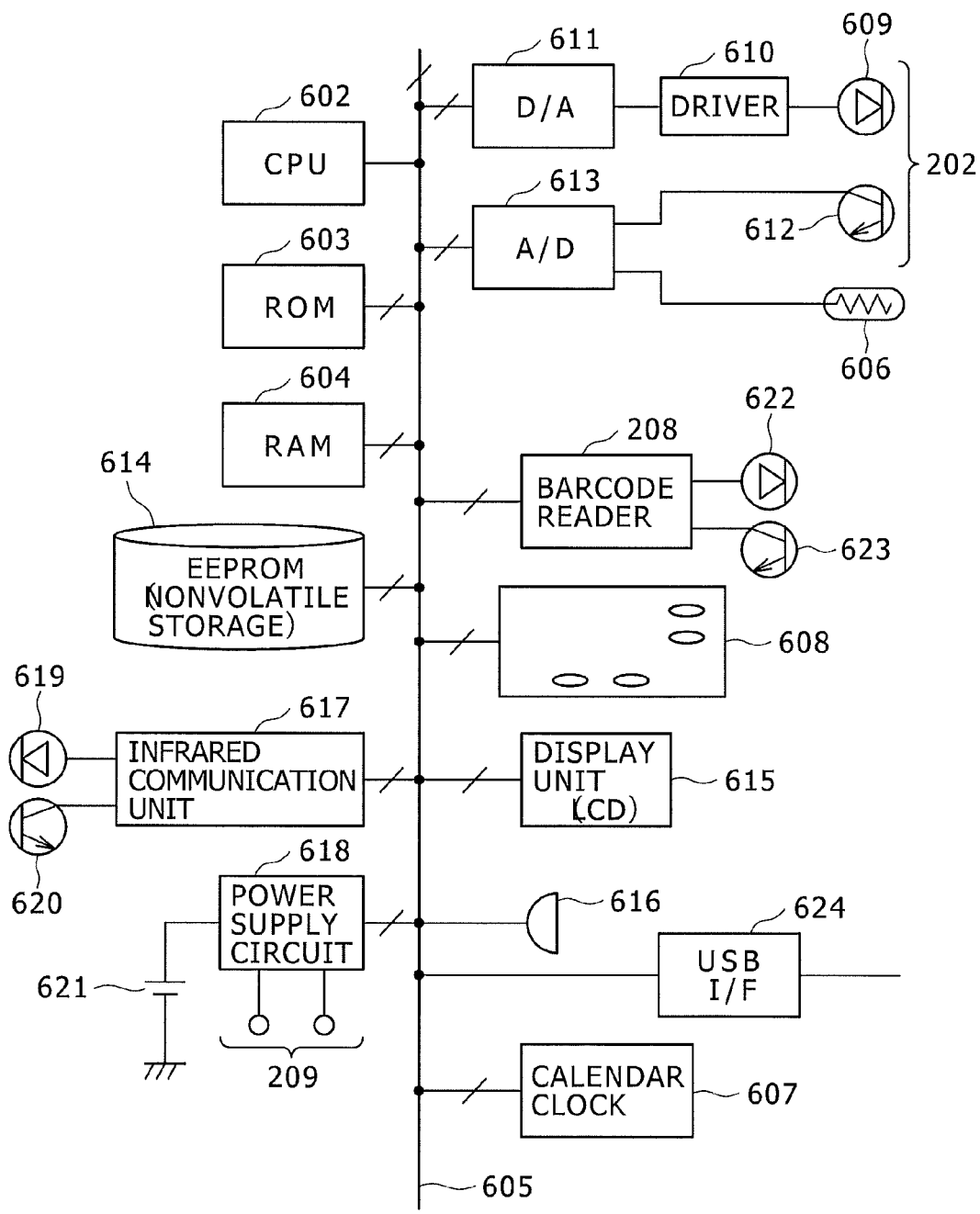
FIG. 3 is an block diagram of the blood glucose meter.

Hardware associated with the blood glucose meter 102 is illustrated in FIG. 3. The blood glucose meter 102 is a system formed from a microcomputer and configured from a CPU 602, a ROM 603, a RAM 604 and a bus 605 which connects the components mentioned to each other. The CPU 602, ROM 603, RAM 604 and bus 605 are components preferably inside the blood glucose meter 102. To the bus 605, also a unit principally for providing a data inputting function and another unit for providing a data outputting function are connected in addition to the components described above.

The data inputting function of the blood glucose meter 102 is provided by the blood glucose level measuring element 202 for obtaining blood glucose level measurement data significant to the blood glucose meter 102, a thermistor 606 for obtaining the temperature data, the barcode reader 208, a calendar clock 607, and an operation unit 608.

The blood glucose level measuring element 202 includes a light emitting unit including a light emitting diode 609, a driver 610 for the light emitting diode 609, and a D/A converter 611 connected to the driver 610, and a light receiving unit including a phototransistor 612 and an A/D converter 613. Since it is necessary for the light emitting diode 609 to irradiate light of an appropriate intensity upon the test paper in the measurement tip 212, the light emitting diode 609 is controlled to emit light based on intensity data stored in advance in a nonvolatile storage 614 hereinafter described. In particular, the emitted light intensity data is read out from the nonvolatile storage 614 and converted into an analog voltage signal by the D/A converter 611 and then power-amplified by the driver 610 to drive the light emitting diode 609 to emit light. Further, an intensity signal voltage of light received by the phototransistor 612 is converted into numerical data by the A/D converter 613. Then, the numerical data obtained by the conversion is recorded into a predetermined region of the RAM 604 and the nonvolatile storage 614.

Further, the blood glucose meter 102 includes the thermistor 606 and can measure the air temperature of the environment in which the blood glucose meter 102 exists depending upon the resistance variation of the thermistor 606. Similar to the phototransistor 612 described above, the resistance value of the thermistor 606 is converted into a numerical value by the A/D converter 613, and the numerical value is recorded into a predetermined region of the RAM 604 and the nonvolatile storage 614. Because there is no need to measure a received light intensity and an air temperature at the same time, the A/D converter 613 is used commonly by the phototransistor 612 and the thermistor 606.

The calendar clock 607 is an IC which provides a well-known date/time data outputting function and is incorporated as a standard component in many microcomputers, personal computers and so forth.

In the blood glucose meter 102 of the embodiment disclosed here, because it is necessary to acquire date/time information of the point of time at which a blood glucose level is measured, the date/time information is important information. In other words, the data to be collected and the date/time information have a very close relationship. And, it is necessary for the date/time information of the point of time at which the blood glucose level is measured to be recorded into the patient table 112 together with the blood glucose level. Therefore, in the figure, the calendar clock 607 is specifically and intentionally provided.

The data outputting function of the blood glucose meter 102 is provided by a display unit 615 formed from the LCD unit 203, a buzzer 616, an infrared communication unit 617 and a USB interface 624.

The ROM 603 is placed in the display unit 615 and displays various screen images depending upon a program executed by the CPU 602.

The buzzer 616 is utilized to notify an operator principally that a barcode has been read normally by the barcode reader 208 or of completion of measurement in blood glucose level measurement, completion of infrared communication or an error message. Depending upon the setting, it is also possible to cause the buzzer 616 to generate sound every time the operation unit 608 is operated.

The infrared communication unit 617 has an infrared light emitting diode 619 and a phototransistor 620 built therein. The infrared light emitting diode 619 and the phototransistor 620 configure an infrared serial communication interface which complies with the well-known IrDA (Infrared Data Association) specifications. Under the control of the CPU 602, the infrared communication function of the infrared communication unit 617 is started up, and transmission/reception of various data files stored in the nonvolatile storage 614 is carried out. The communication unit 617 is an example of a communication means which determines, in connection with each blood glucose levels recorded in the measurement data table, a string of transmission data (e.g., the patient identification information, the blood glucose level, the date/time information indicating the date and time at which the blood glucose level is obtained, and mode information), in which a non-recorded item is determined as blank information, and transmits the transmission data to an external apparatus such as the measurement data management apparatus.

The elements which configure the internal microcomputer of the blood glucose meter 102 include the nonvolatile storage 614 formed from an EEPROM which provides a data storage function in addition to the data inputting and outputting functions. Into this nonvolatile storage 614, user base data 115, tip lot data 116, patient data table 112, a measurement data table 118, blood glucose meter setting data and so forth are stored. They are updated upon communication with the measurement data management apparatus 104 through the USB cable 105 or the infrared communication function described hereinabove. A flash memory or the like may be used in place of the EEPROM. In the patient data table 112, in order to identify a patient by the identification means, patient IDs and information with which the patients can be identified such as the patient name, sex, date of birth and so forth are stored in advance in an associated relationship with each other. Further, in the measurement data table, a measured blood glucose level and time at which the blood glucose level is obtained are stored in an associated relationship with information useful for medical practice such as, for example, a patient ID.

[Measurement Data Management Apparatus 104]

Figure 4:
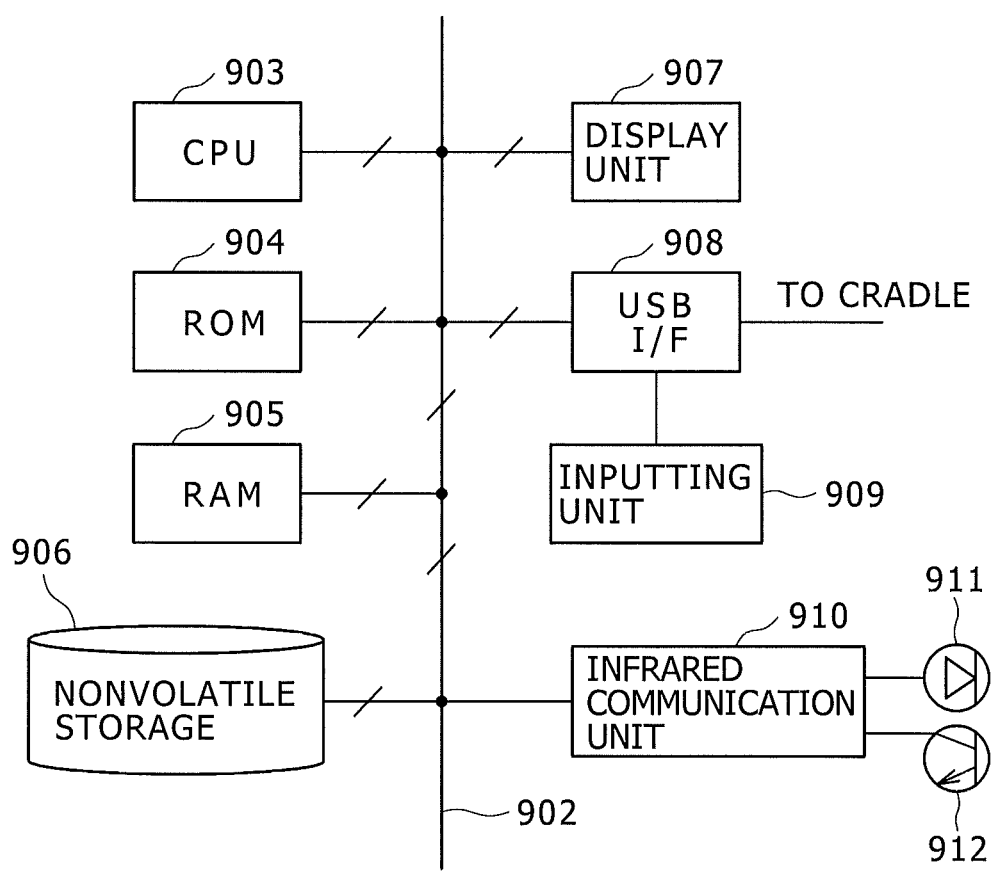
FIG. 4 is a block diagram of a measurement data management apparatus.

Aspects of the measurement data management apparatus 104 are illustrated in FIG. 4. The entity of the measurement data management apparatus 104 is also a well-known personal computer, and hardware which has a special function is not provided when various alarming functions hereinafter described, a function for managing measurement and so forth are implemented by the present embodiment.

A bus 902 is provided in the inside of the measurement data management apparatus 104 which is a personal computer. To this bus 902, a CPU 903, a ROM 904, a RAM 905, a nonvolatile storage 906 such as a hard disk apparatus, a display unit 907 such as an LCD unit, and a USB interface 908 are connected. To the USB interface 908, an inputting unit 909 such as a keyboard, a mouse and so forth is connected. Further, the bus 902 includes an infrared communication unit 910. The infrared communication window of the blood glucose meter 102 and the infrared communication unit 910 of the measurement data management apparatus 104 have infrared light emitting diodes 619 and 911 and phototransistors 620 and 912 built therein, respectively. They configure an infrared serial communication interface which complies with the well-known IrDA (Infrared Data Association) specifications. The communication unit 910 is an example of a host communication means for communicating with the communication unit 617.

[Blood Glucose Measuring Operation of the Blood Glucose Meter 102]

Figure 5:
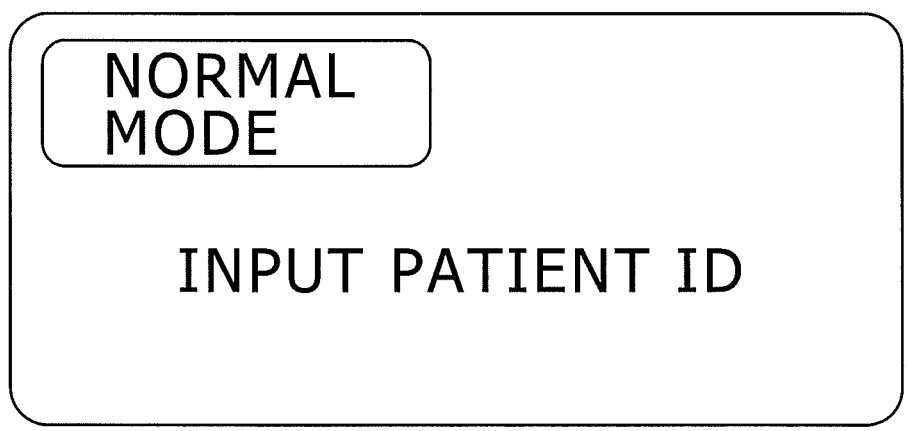
FIG. 5 is an example of the display of the blood glucose meter in a normal measurement mode.

Now, a blood glucose measuring operation in a normal measurement mode carried out by the blood glucose meter 102 is described. If the power supply switch is switched on and the start button 205 is depressed to select the normal measurement mode, then "Normal mode" is displayed on the LCD unit 203 as seen in FIG. 5. This normal measurement operation is performed under the control of the CPU 903 so that the CPU 903 is an example of a control means which operates in the normal measurement mode to, for example, cross-check the patient identification information and the patient data table, and permit blood glucose level measurement if the patient identification information is found.

(1) A patient ID (patient identification information) in the form of a barcode applied to a name tag or the like of a patient is read by the barcode reader 208.

The read patient ID is used first as a search key of the patient data table 112.

Patient data 114 transmitted in advance from the measurement data management apparatus 104 is converted into a patient data table 112 in the inside of the blood glucose meter 102 and stored into the nonvolatile storage 614. This patient data table 112 is searched with the patient ID. If a hit record is found in the search, then this patient ID is recorded into a blank record of the measurement data table 118.

(2) Then, a user ID in the form of a barcode applied to a name tag or the like of a nurse is read by the barcode reader 208.

It is verified whether or not the read user ID is included in the user base data 115. The user base data 115 is searched using the user ID as a search key, and if the user ID exists, then this is recorded into a "user ID" field of the record of the measurement data table into which the patient ID was recorded formerly.

(3) Then, a tip lot number in the form of a barcode printed on a box and so forth of the measurement tip 212 is read by the barcode reader 208.

It is verified whether or not the read tip lot number is included in the tip lot data 116 (refer to FIG. 1). If the tip lot data 116 is searched using the tip lot number as a search key and the tip plot number exists, then it is recorded into a "tip lot number" field of the formerly specified record of the measurement data table 118.

(4) Immediately after the tip plot number is recorded into the "tip lot number" field of the measurement data table 118 in (3), the external air temperature is measured by the thermistor 606. Then, if it is decided that the external air temperature is included within a predetermined range, then it is recorded into a "temperature upon measurement" field of the formerly specified record of the measurement data table 118.

(5) A measurement tip 212 is mounted on the blood glucose level measuring portion of the blood glucose meter 102 to measure the blood glucose level. Then, date/time data of the point of time at which the blood glucose level is measured is acquired from the calendar clock 607. The calendar clock 607 thus serves as a time counting means which obtains date and time information at which the blood glucose level is obtained by the blood glucose level measuring meter 102.

The measured blood glucose level is recorded into a "blood glucose level" field of the formerly specified record of the measurement data table 118. The date/time data is recorded into a "measurement date/time" field of the formerly specified record of the measurement data table 118.

Further, a flag representative of a "fact" that a "blood glucose level was measured" is recorded into a "measurement-display-dose flag" field.

Thereafter, the measured blood glucose level, patient ID, patient name and measurement date/time are displayed on the LCD unit 203 (display unit 615).

(6) A sliding scale of the patient is searched out using the measured blood glucose level, and a kind of a medicine such as insulin and a dosage amount of the medicine to be prescribed for the patient are displayed on the LCD unit 203. The sliding scale is stored for each patient ID in the patient data table 112.

(7) After the nurse carries out dosage of insulin or the like in accordance with the prescription displayed on the LCD unit 203, this fact is inputted by depressing the start button 205. Consequently, a flag representative of the "fact" that insulin or the like is "prescribed" is recorded into the "measurement-display-dose flag" field of the measurement data table 118.

By the measuring operation described above, the following are recorded into the measurement data table 118:
  at what scheduled time
  for which patient,
  which measuring person
  uses a tip of which tip lot number,
  in an environment of what external air temperature,
  to measure or not to measure the blood glucose level,
  (if the blood glucose level is measured) what value the blood glucose level exhibits,
  (if the blood glucose level is measured) what is the date/time,
  whether or not insulin or the like is prescribed.

The blood glucose level measuring operation and the insulin prescribing operation are carried out within a generally fixed time slot after a meal of a patient. Or, they may be carried out within a fixed time slot before a meal. The measuring operation and the prescribing operation are carried out collectively within a fixed time slot for a plurality of patients.

The operation unit of the blood glucose level measurement and/or insulin prescription carried out collectively within a predetermined time slot for a plurality of patients is called "round." For example, the operation unit is called "one round for 30 minutes after breakfast" or the like and handled.

In order to prevent the blood glucose meter 102 from making a mistake in the blood glucose level measuring operation and the prescribing operation of insulin or the like, only data necessary for one round is transmitted from the measurement data management apparatus 104 to the blood glucose meter 102. That data is the patient data 114, user base data 115 and tip lot data 116.

Then, after the round comes to an end, the blood glucose meter 102 is connected to the measurement data management apparatus 104 by the USB cable 105 or through the infrared communication window and the measurement data table 118 is transmitted from the blood glucose meter 102 to the measurement data management apparatus 104 without fail. The measurement data management apparatus 104 receives this and records it into a patient history table 1212 thereof.

[Blood Glucose Measuring Operation in the Emergency Measurement Mode]

Figure 6:
FIG. 6 is an example of the display of the blood glucose meter in an emergency measurement mode.

Now, a flow of the blood glucose measuring operation in the emergency measurement mode carried out by the blood glucose meter 102 is described. This emergency measurement operation is performed under the control of the CPU 903 so that the CPU 903 operates as a control means which operates in the emergency measurement mode to, for example, permit measurement of the blood glucose level even though patient identification information is not acquired. In the emergency measurement mode, cross-checking of a patient ID is not required. However, the blood glucose measuring function may be configured such that it does not require any of cross-checking of a user ID or a tip lot number and recording of a fact of insulin prescription. In the present working example, a blood glucose measuring operation in the case where collection of a user ID and a tip lot number and recording of a fact of insulin prescription are carried out is described. If a confirmation power supply switch is switched on and then the emergency button 206 is depressed to select the "emergency measurement mode," then "Emergency mode" is displayed on the LCD unit 203 as seen in FIG. 6. This display of "Emergency mode" on the LCD unit is a notification means providing a notification that the current mode is the emergency measurement mode or is not the normal measurement mode.

(1) When the emergency button 206 is depressed, a blank record of the measurement data table 118 is specified without a patient ID.

(2) Then, a user ID in the form of a barcode applied to a name tag or the like of a nurse is read by the barcode reader 208.

It is verified whether or not the read user ID is included in the user base data 115. If the user base data 115 is searched using the user ID as a search key and the user ID exists, then it is recorded into the "user ID" field of the record of the measurement data table 118 into which the patient ID has been recorded formerly.

(3) Then, a tip lot number in the form of a barcode printed on a box or the like of the measurement tip 212 is read by the barcode reader 208.

It is verified whether or not the read tip lot number is included in the tip lot data 116 (refer to FIG. 1). If the tip lot data 116 is searched using the tip lot number as a search key and the tip lot number exists, then it is recorded into the "tip lot number" field of the formerly specified record of the measurement data table 118.

(4) Just after the tip lot number is recorded into the "tip lot number" field of the measurement data table 118 in (3), the external air temperature is measured by the thermistor 606. Then, if it is decided that the external air temperature is included within a predetermined range, then it is recorded into the "temperature upon measurement" field of the formerly specified record of the measurement data table 118.

(5) A measurement tip 212 is mounted on the blood glucose level measuring portion of the blood glucose meter 102 to measure the blood glucose level. Then, date/time data of the point of time at which the blood glucose level is measured is acquired from the calendar clock 607.

The measured blood glucose level is recorded into the "blood glucose level" field of the formerly specified record of the measurement data table 118. The date/time data is recorded into the "measurement date/time" field of the formerly specified record of the measurement data table 118.

Further, the flag representative of the "fact" that a "blood glucose level has been measured" is recorded into the "measurement-display-dosage" field.

Thereafter, the measured blood glucose level, measurement date/time and "emergency mode" are displayed on the LCD unit 203 (display unit 615).

(6) After the nurse carries out dosage of insulin or the like, by depressing the start button 205, a flag representative of the "fact" that insulin has been "prescribed" is recorded into the "measurement-display dosage flag" field of the measurement data table 118.

By the measuring operation described above, the following are recorded into the measurement data table 118
  which measuring person
  uses a tip of which tip lot number,
  in an environment of what external air temperature,
  to measure or not to measure the blood glucose level,
  (if the blood glucose level is measured) what value the blood glucose level exhibits, (if the blood glucose level is measured) what is the date/time, whether or not insulin or the like is prescribed.

The measuring operation in the emergency measurement mode has thus far described above. Although the "user ID," "tip lot number," "fact of insulin preservation" and so forth may be omitted as described above, it is necessary to record the "blood glucose level" and the "measurement date/time" without fail. Here, such setting may be used that the "user ID," "tip lot number," "fact of insulin preservation" and so forth may be additionally recorded later similarly to additional recording of a patient ID hereinafter described.

[Display of the History]

Set forth next is a description of the operation for displaying a history of data recorded in the blood glucose meter 102. A history display mode is entered by depressing the History button 207 in the normal measurement mode.

(1) The history button 207 is depressed to advance to a display screen image for a history of the blood glucose level measured in the normal measurement mode, and a patient ID is inputted in order to determine the history of which patient should be displayed. The input of the patient ID is carried out by reading a patient ID in the form of a barcode applied to a name tag or the like of the patient by means of the barcode reader 208. Or another method may be used wherein a list of patient IDs and patient names recorded in the patient data table may be displayed on the LCD unit 203 to carry out selection. Or, a keypad may be displayed on the LCD unit 203 such that a patient ID and a patient name may be inputted through the keypad displayed on the LCD unit 203.

(2) After a patient ID is inputted, from among data recorded in the measurement data table 118 or the patient data table 112 and associated with the patient ID, the blood glucose level of the latest data and information of the date/time at which the blood glucose level is obtained are displayed on the LCD unit 203. Further, some other information such as the patient ID, patient name or user name may be displayed additionally. Furthermore, an average value of the blood glucose levels associated with the patient ID recorded in the measurement data table and a plurality of blood glucose levels backdating time-sequentially or the like may be displayed.

(3) Then, by depressing the history button 207, time-sequentially subsequent new data associated with the patient ID is displayed.

(4) On the other hand, if the start button 205 is depressed, then the history of a new patient can be displayed.

(5) By depressing the power supply button 204 to turn off the power supply, the operation in the history display mode is ended.

[Display of a History of Data Measured in the Emergency Measurement Mode and Additional Recording of a Patient ID]

Figure 7:
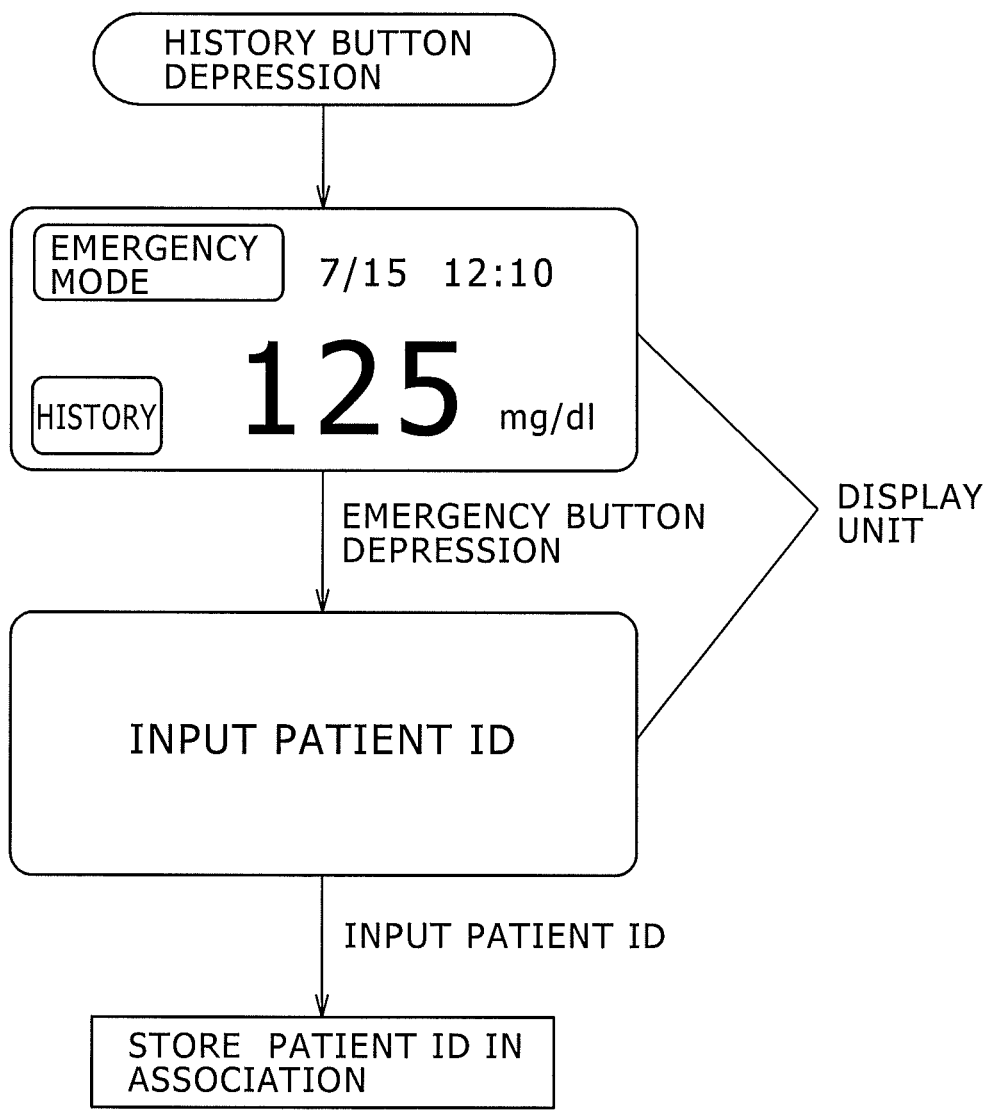
FIG. 7 is a flow chart illustrating an example of association with a patient ID in the emergency measurement mode of the blood glucose meter.

Now, display of a history of data measured in the emergency measurement mode and recorded in the blood glucose meter 102 and a later inputting operation of a patient ID are described. By depressing the history button 207 in the emergency measurement mode, such display and inputting operation are entered (FIG. 7).

(1) By depression of the history button 207, a history of blood glucose levels measured in the emergency measurement mode is transferred so as to be displayed in a display screen image. Thus, the blood glucose level of the latest data from among those data with regard to which the emergency measurement flag recorded in the measurement data table 118 is "ON" and the patient ID data is blank and information of the date/time at which the blood glucose level is obtained are displayed on the LCD unit 203. Further, some other information such as the user name may be displayed additionally.

(2) Then, by depressing the history button 207, time-sequentially subsequently new data from among data with regard to which the emergency measurement flag recorded in the measurement data table 118 is "ON" and the patient ID data is blank are displayed. (3) On the other hand, if the emergency button 206 is depressed, then inputting of a patient ID is demanded in order to associate the displayed data with a patient ID for later reference. As inputting of a patient ID, the patient ID in the form of a barcode applied to a name tag or the like of the patient is read by means of the barcode reader 208. Or, a keypad may be displayed on the LCD unit 203 such that a patient ID or a patient name may be inputted through the keypad displayed on the LCD unit 203.

(4) After a patient ID is inputted, the inputted patient ID is overwritten as the displayed data into the measurement data table 118 through a confirmation screen image of the inputted data or the like.

(5) The processing is ended by depressing the power supply button 204 to turn off the power supply.

Figure 8:
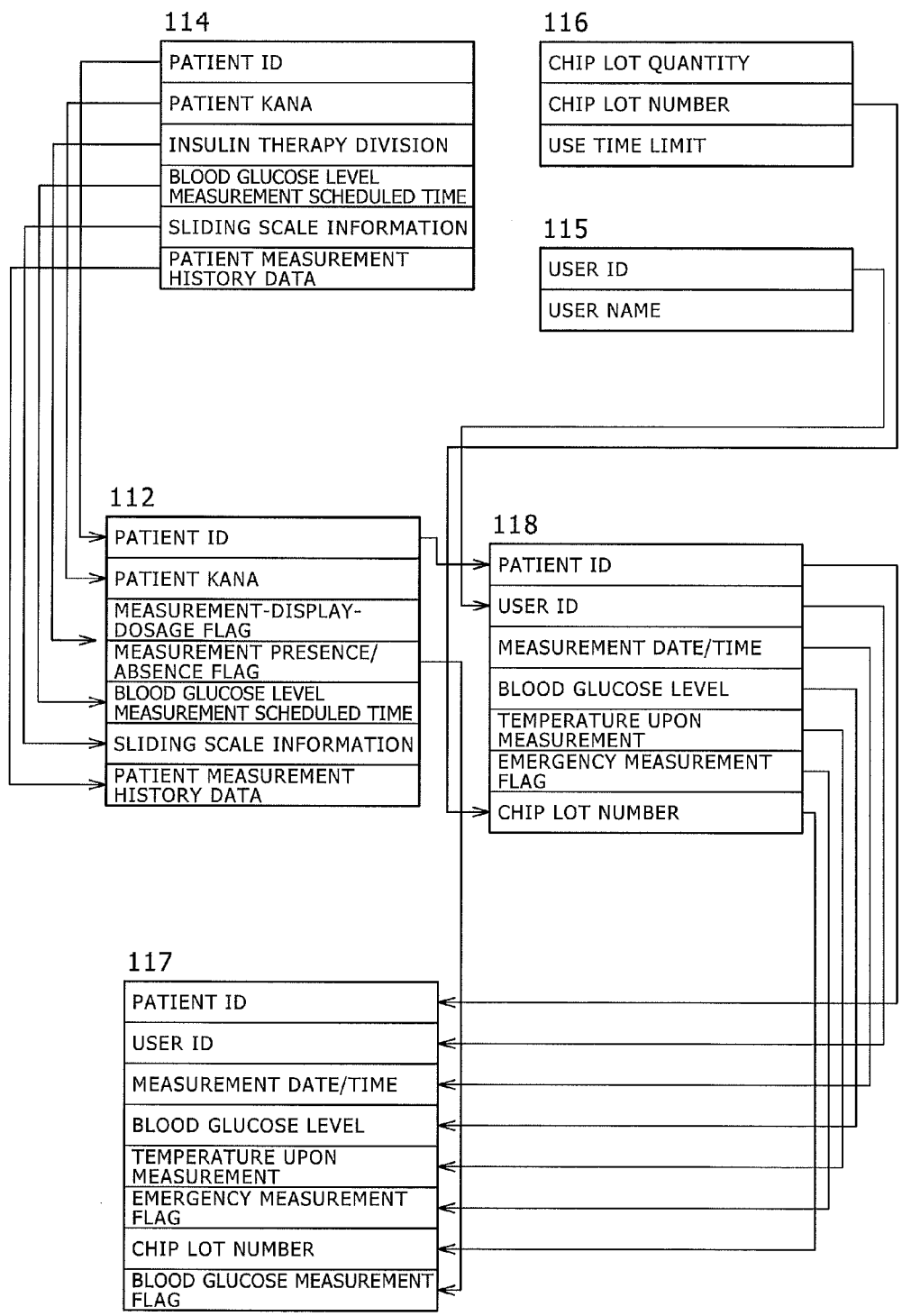
FIG. 8 is a view illustrating an internal configuration of and a relationship among tables.

FIG. 8 is a view illustrating an internal configuration of and a relationship among the tables. FIG. 8 is drawn based on the relationship of the tables transmitted and received between the measurement data management apparatus 104 and the blood glucose meter 102 shown in FIG. 1.

The patient data 114 transmitted from the measurement data management apparatus 104 are recorded into the patient data table 112 in regard to all fields thereof other than the "insulin therapy segment" field. The patient data table 112 is provided in the nonvolatile storage 614 in the inside of the blood glucose meter 102.

The "insulin therapy segment" field of the patient data 114 is recorded into the "measurement-display-dosage flag" field and the "measurement presence/absence flag" field of the patient data table 112 through a predetermined conversion process.

Tip lot data 116 and user base data 115 transmitted from the measurement data management apparatus 104 are recorded as they are into the nonvolatile storage 614 in the inside of the blood glucose meter 102. Then, those (the tip lot number and the user ID) read from the barcode reader 208 during the measuring operation are recorded every time into the measurement data table 118 together with the patient ID.

[Patient Data 114]

Now, the fields of the patient data 114 are described. In the "insulin therapy segment" field of the patient data 114, one of
0: only blood glucose level measurement
1: blood glucose level measurement+insulin dosage using sliding scale
2: blood glucose level measurement+insulin dosage without using sliding scale (hereinafter referred to as "fixed" insulin dosage)
5: only insulin dosage using sliding scale (without blood glucose level measurement)
6: only fixed insulin dosage (without blood glucose level measurement) is recorded.

The sliding scale signifies "recipe" data. This is a table which lists amounts of an agent such as insulin to be dosed with respect to a range of measured blood glucose levels.

"Fixed" dosage signifies to dose a fixed amount of an agent such as insulin irrespective of a result of measurement of the blood glucose level.

In the "sliding scale information" field of the patient data 114, this sliding scale is stored.

The value of the "insulin therapy segment" field of the patient data 114 is flag information indicative of an operation to be carried out for each patient with respect to the blood glucose meter 102. For example:

if the value is "0," then only measurement of the blood glucose level is carried out for the patient;

if the value is "1," then measurement of the blood glucose level and insulin dosage using the sliding scale are carried out for the patient.

This similarly applies also to "2," "5" and "6."

The value of the "patient ID" field is a number for identifying a patient and is recoded on a barcode applied to clothes or the like of the patient. The "patient kana" field indicates phonetic transcriptions by katakana of the name of the patient. This is displayed on the LCD unit 203 of the blood glucose meter 102 together with the patient ID and used by a measuring person, who operates the blood glucose meter 102, to correctly identify the patient in front of the measuring person.

The "blood glucose measurement scheduled time" field represents time at which it is scheduled to carry out a round and is used also as a search key for specifying data by the measurement data management apparatus 104 side.

The "patient measurement history data" is a field in which a plurality of pieces of the latest blood glucose level measurement history information of the patient is stored. Further, when the value of the "insulin therapy segment" field is "5," a blood glucose level measured latest is stored, and insulin dosage using a sliding scale is carried out based on this value.

The foregoing is description of the fields of the patient data 114.

[Patient Data Table 112]

Now, the fields of the patient data table 112 are described. The "measurement-display-dosage flag" field is a field in which three flags including the "blood glucose level measurement flag," "insulin dosage amount display flag" and "insulin dosage confirmation flag" are stored.

In the "measurement presence/absence flag" field, when the "insulin therapy segment" field of the patient data 114 is "0," "1" or "2," "1" representing "true" of the logic, but when the insulin therapy segment field of the patient data 114 is "5" or "6," "0" representing "false" of the logic is recorded.

The measurement-display-dosage flag" field changes (1) immediately after a blood glucose level measuring operation is completed, (2) when an insulin dosage amount is displayed, and (3) when it is inputted that insulin dosage has been carried out.

The contents of the "measurement-display-dosage flag" field and the "measurement presence/absence flag" field are reflected on the "blood glucose measurement flag" field of patient measurement data 117.

The "patient ID" field, "patient kana" field, "blood glucose measurement schedule time" field, "sliding scale information" field and "patient measurement history data" field are copied from the patient data 114.

[Measurement Data Table 118]

Into the "patient ID" field, a patient ID read by the barcode reader 208 is recorded. In the case of the emergency measurement mode, the "patient ID field" is a blank field.

Into the "user ID" field, a user ID read by the barcode reader 208 is recorded after cross-checking by the user base data 115.

Into the "tip lot number" field, a tip lot number read by the barcode reader 208 is recorded after cross-checking by the tip lot data 116.

Values of the "measurement date/time" field, "blood glucose level" field and "measurement-time temperature" field are recorded upon a blood glucose level measuring operation of the blood glucose meter 102.

In the "emergency measurement flag," "1" is recorded by turning the flag ON with regard to blood glucose level data measured in the emergency measurement mode whereas "0" is recorded by turning the flag OFF with regard to blood glucose level data measured in the normal measurement mode.

As described hereinabove, in the normal measurement mode, the blood glucose meter 102 records a blood glucose level, time at which the blood glucose level is obtained and a patient ID into the measurement data table 118, but in the emergency measurement mode, the blood glucose meter 102 does not record the patient ID. Then, in order to distinguish the data measured in the normal measurement mode and the data measured in the emergency measurement mode from each other, the flag representative of whether the measurement mode is the emergency mode is recorded as OFF in the normal measurement mode but as ON in the emergency measurement mode. Blood glucose levels obtained in the normal measurement mode and the emergency measurement mode and records of time at which the blood glucose levels are obtained exist in a mixed state.

[Patient Measurement Data 117]

The contents of the "measurement-display-dosage flag" field and the "measurement presence/absence flag" field of the patient data table are outputted as data of the "blood glucose measurement flag" field after a predetermined conversion process.

Further, the data of the measurement data table 118 are outputted as they are to the measurement data management apparatus 104.

[Data Transfer from the Blood Glucose Level Measuring Apparatus to the Measurement Data Management Apparatus]

Figure 9:
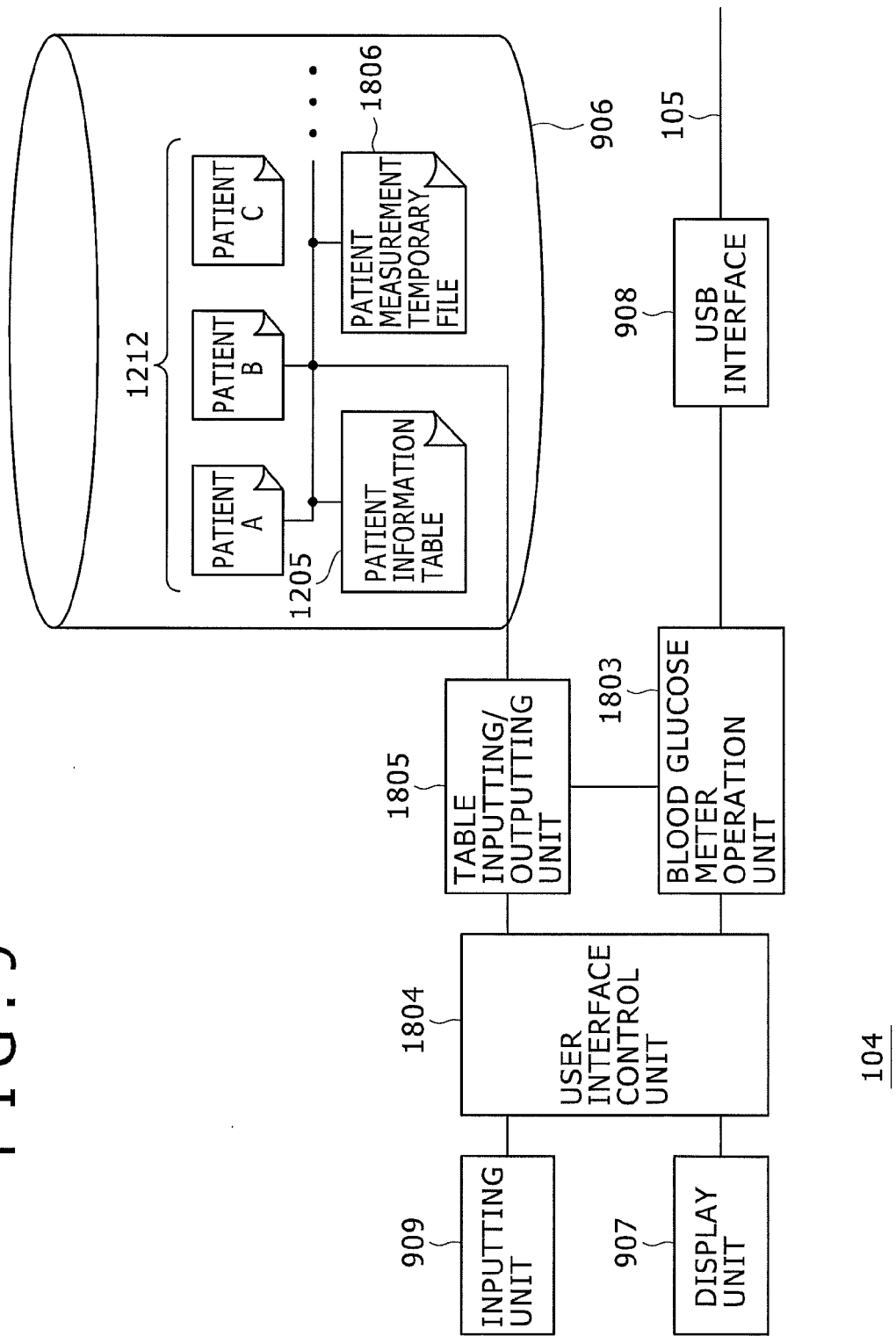
FIG. 9 is a functional block diagram of the measurement data management apparatus.

The blood glucose meter 102 and the measurement data management apparatus 104 carry out data communication with each other through the USB cable 105 or through the infrared communication window. The measurement data management apparatus 104 records the contents of the received patient measurement data 117 into the patient history table 1212 (FIG. 9). Thereupon, the patient measurement data 117 is recorded into a patient measurement temporary file 1806, and if the patient ID is not blank or absent, then cross-checking between the contents recorded in the patient history table 1212 formed from files for individual patients and the contents recorded formerly in a patient information table 1205 is carried out using a patient ID in one measurement data string of the patient measurement data file as a search key. Further, in the case where the patient ID is blank, the one measurement data string is left as it is in the temporary file.

If, as a result of the cross-checking operation, there is no mismatch between the indication contents and the execution result with regard to all patients whose patient ID is not blank, then the measurement data management apparatus 104 displays "OK" on the display unit 907 thereof.

On the other hand, after the blood glucose meter 102 transfers the patient measurement data 117 to the measurement data management apparatus 104, it deletes the data of the patient data table 112. By this action, the blood glucose meter 102 can always guarantee to carry out blood glucose level measurement or insulin dosage based only on the latest data.

In the blood glucose meter 102, only data of a patient which becomes an object for which one round is to be carried out and measurement data in the emergency measurement mode ready for emergency generated within the round are stored.

If it has failed to carry out blood glucose level measurement or insulin dosage for some patient, then the measurement data management apparatus 104 verifies the received patient measurement data to specify the patient for which blood glucose level measurement or insulin dosage has not been carried out. Then, with regard to the specified patient, only data for a necessary treatment to be carried out are produced again. In other words, a "re-round" is carried out.

The design of "to execute only one round" of the blood glucose meter 102 is based on the concept that an error in blood glucose level measurement or insulin dosage shall not be caused at all.

Further, also in the case where emergency measurement is carried out, since emergency measurement data is not accumulated for a long period of time in the blood glucose level measuring apparatus, association between data in the emergency measurement mode and a measured patient does not become difficult at all.

Figure 10:
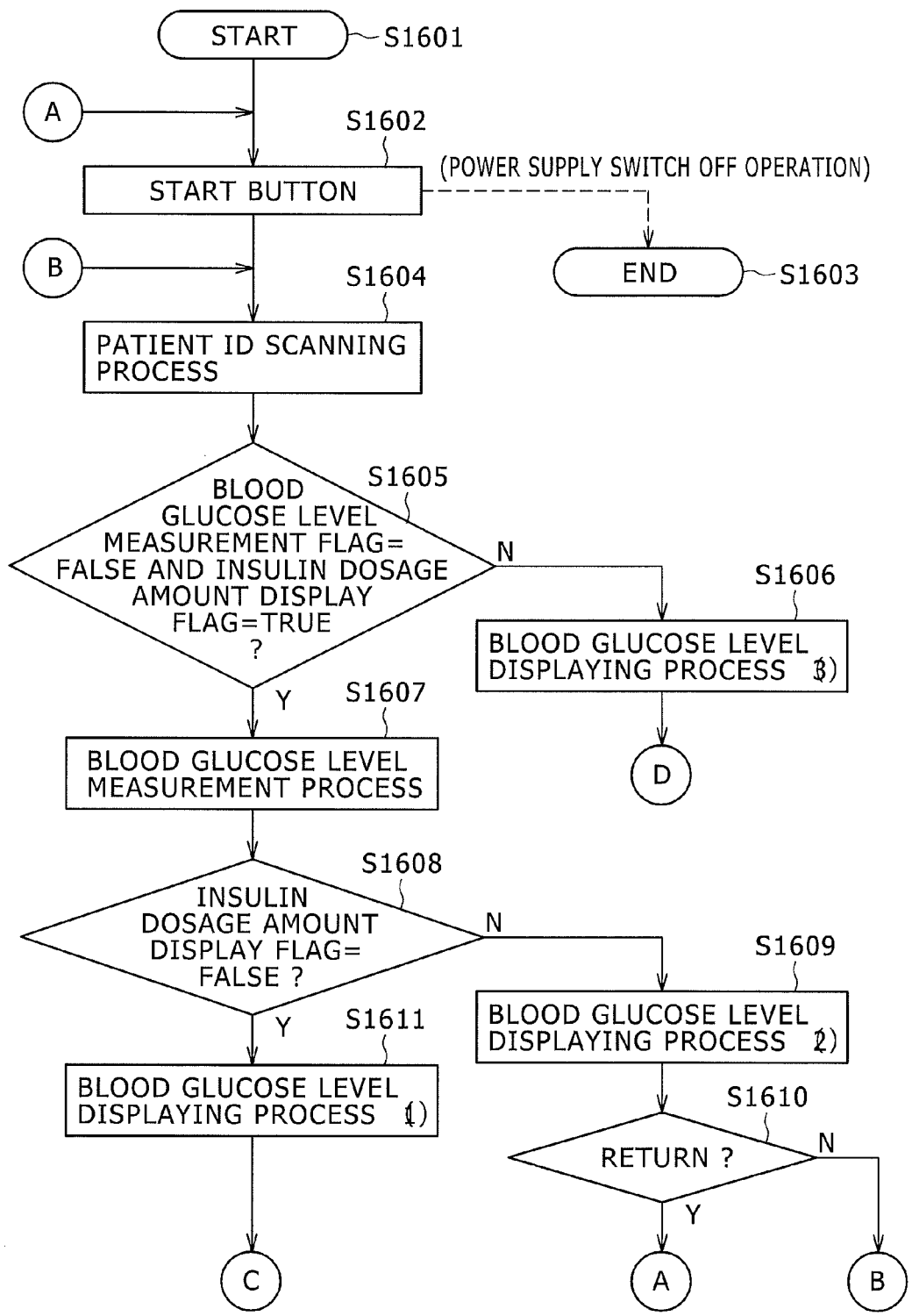
FIG. 10 is a flow chart illustrating a flow of processing of the blood glucose meter.
Figure 11:
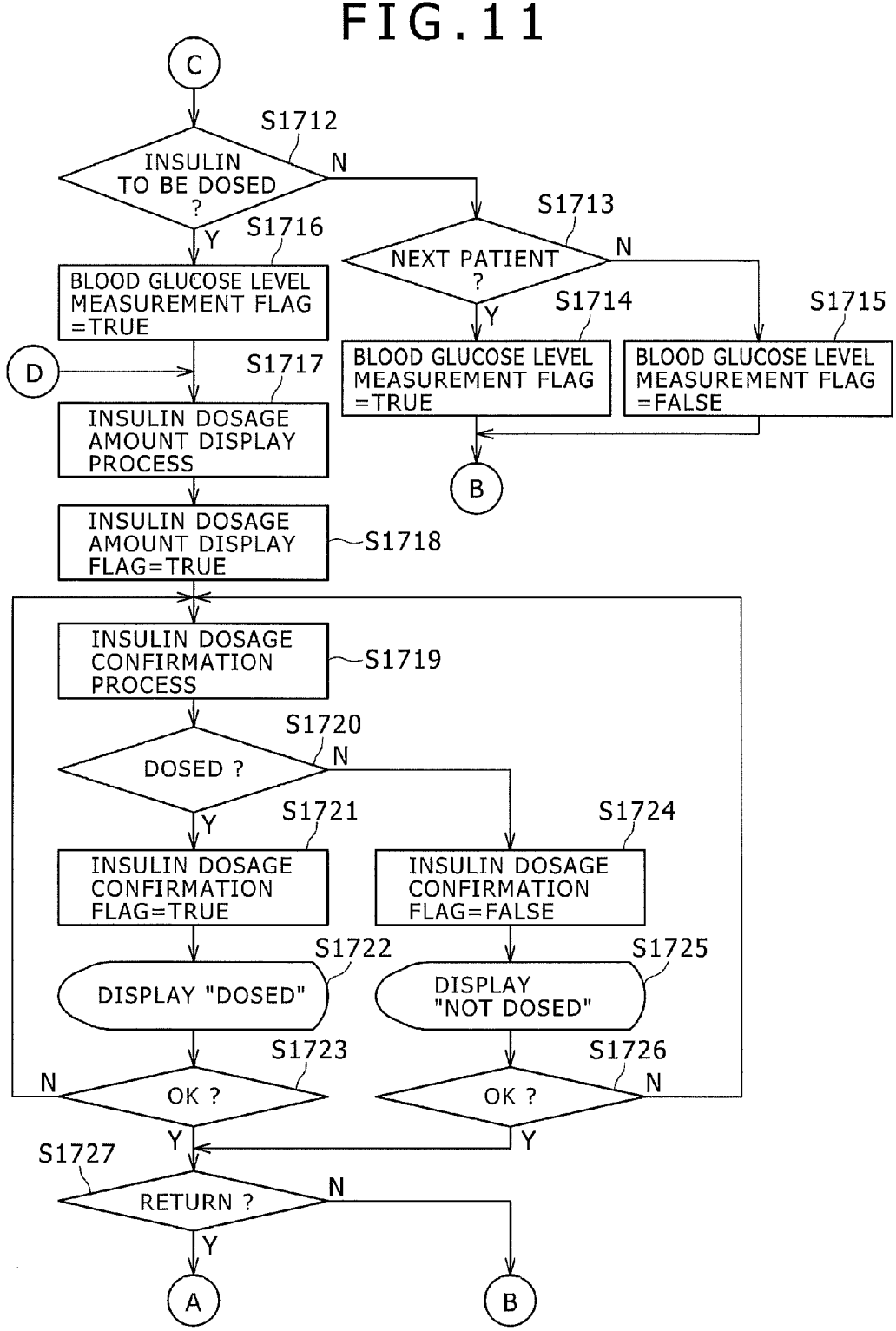
FIG. 11 is a flow chart illustrating a flow of processing of the blood glucose meter.

FIGS. 10 and 11 are flow charts illustrating a flow of processing of the blood glucose meter 102.

The processing is started by switching on the power supply button 204 (S1601). In order to select the normal measurement mode, the start button 205 on the blood glucose meter 102 is depressed first (S1602). Here, if the power supply button 204 is operated into an off state, then the processing is ended (S1603).

If the depression (S1602) of the start button 205 comes to an end, then the blood glucose meter 102 carries out a patient ID scanning process of reading a patient ID by way of the barcode reader 208 (S1604).

After the patient ID is read by the patient ID scanning process (S1604), an inputting/outputting control unit checks the blood glucose level measurement flag and the insulin dosage amount display flag included in the record of the relevant patient ID of the patient data table 112 (S1605). Here, in the case where the blood glucose level measurement flag is true and besides the insulin dosage amount display flag is false (N of S1605), then the blood glucose meter 102 carries out a blood glucose level displaying (3) process (S1606). In any other case, that is, in the case where the blood glucose level measurement flag is false or the insulin dosage amount display flag is true (Y of S1605), the blood glucose meter 102 carries out a blood glucose level measurement process (S1607).

After measurement of the blood glucose level is carried out by the blood glucose level measuring process (S1607), the inputting/outputting control unit 1402 subsequently carries out confirmation of the insulin dosage amount display flag (S1608). If the insulin dosage amount display flag is false (Y of S1608), then the blood glucose meter 102 carries out a blood glucose level displaying (1) process (S1611). In the other case, that is, in the case where the insulin dosage amount display flag is true (N of S1608), the blood glucose meter 102 carries out a blood glucose level displaying (2) process (S1609).

Description is Continued with Reference to FIG. 11.

After the blood glucose meter 102 ends the blood glucose level displaying (1) process (S1611), it advances to a next state in response to an operation of the user.

In the case where blood glucose level measurement is to be carried out again (N of S1712 and N of S1713), then the blood glucose level measurement flag of the relevant patient is left false (S1715) and the processing returns to the patient ID scanning process (S1604).

In the case where insulin dosage treatment for the patient with regard to which the blood glucose level is not measured and the processing advances to a blood glucose level measurement of a next patient (N of S1712 and Y of S1713), the blood glucose level measurement flag of the relevant patient is set to true (S1714), and then the processing returns to the patient ID scanning process (S1604).

In the case where insulin dosage treatment for the patient with regard to which the blood glucose level is measured at present (Y of S1712), the blood glucose level measurement flag of the relevant patient is set to true (S1716), and then an insulin dosage displaying process is carried out (S1717).

After the blood glucose level displaying (3) process (S1606) comes to an end, the blood glucose meter 102 displays the blood glucose level of the patient. Thereafter, the blood glucose meter 102 carries out an insulin dosage amount displaying process (S1717).

In the insulin dosage amount display process (S1717), the blood glucose meter 102 displays the insulin dosage amount to the patient in accordance with the contents of the patient table 112. After this displaying process is carried out, the inputting/outputting control unit 1402 sets the insulin dosage amount display flag to true (S1718) and carries out an insulin dosage confirmation process (S1719).

In the insulin dosage confirmation process (S1719), the blood glucose meter 102 waits inputting for issuing an inquiry regarding whether or not insulin dosage is carried out to the user.

If it is inputted that the user has carried out insulin dosage as a result of an operation of the operation unit 608 by the user (Y of S1720), then the inputting/outputting control unit 1402 sets the insulin dosage confirmation flag to true (S1721), and display of "dosed" is carried out (S1722). Then, in order to make it possible to carry out inputting again, a confirmation input is accepted (S1723), and if any other choice than "return" (N of S1723) is selected (Y of S1723), then the processing returns to the start (Y of S1727) or the processing is started with the patient ID scanning process (N of S1727) in accordance with a result of the selection (S1727).

If the user inputs that insulin dosage has not been carried out as a result of the operation of the operation unit 608 by the user (N of S1720), then the inputting/outputting control unit 1402 sets the insulin dosage confirmation flag to false (S1724) and display of "not dosed" is carried out (S1725). Then, in order to make it possible to carry out inputting again, a confirmation input is accepted (S1726). Then, if any other choice than "return" (N of S1726) is selected (Y of S1726), the processing returns to the start (Y of S1727) or the processing begins with the patient ID scanning process (N of S1727) in accordance with a result of the selection (S1727).

FIG. 9 illustrates features of the measurement data management apparatus 104.

Although the measurement data management apparatus 104 is provided with various functions in addition to the functions discussed below in connection with the present embodiment, the present embodiment is described only in connection with the functions which relate to cross-checking between the patient information table 1205 and the patient history table 1212.

A blood glucose meter operation unit 1803 carries out an operation of the measurement data management apparatus 104 to collect patient measurement data 117 and so forth from the blood glucose meter 102 and to transmit the patient data 114 and so forth to the blood glucose meter 102.

The inputting unit 909 includes a keyboard, a mouse and so forth. The display unit 907 includes an LCD display unit or the like. The inputting unit 909 and the display unit 907 are connected to a user interface control unit 1804.

The user interface control unit 1804 displays a predetermined operation screen image on the display unit 907. Further, the user interface control unit 1804 receives an operation of a user from the inputting unit 909 to change the operation screen image to be displayed on the display unit 907 or to input/output necessary data from a table inputting/outputting unit 1805.

The table inputting/outputting unit 1805 is an interface which carries out inputting and outputting of data between many tables such as the patient history table 1212, patient information table 1205, and patient measurement temporary file 1806, which are stored in the nonvolatile storage 906 of the measurement data management apparatus 104, and the user interface control unit 1804 and blood glucose meter operation unit 1803. In particular, the table inputting/outputting unit 1805 is a database manager called middleware.

It is necessary for the measurement data management apparatus 104 to retain a large amount of data. Particularly since the measurement data table 118 is downloaded from the blood glucose meter 102 and retained into the nonvolatile storage 906 every time a round comes to an end, the data amount increases day by day. In order to implement a rapid data inputting and outputting function for such a large amount of data as just described, preferably the middleware exists.

Further, when a program is constructed, if middleware exists, then the production efficiency is improved.

It is to be noted that, while, in FIG. 9, only the patient history table 1212 and the patient information table 1205 are shown, actually a greater number of tables exist. In FIG. 8, the presence of tables which are not necessary for description of the present embodiment is omitted.

The patient history table 1212 is produced for each patient. Therefore, the table names of the patient history tables 1212 individually include patient IDs. This is a result of taking the efficiency of data storage into consideration. It is to be noted that also it is possible to configure the tables into a single table which includes a field for patient IDs.

Figure 12:
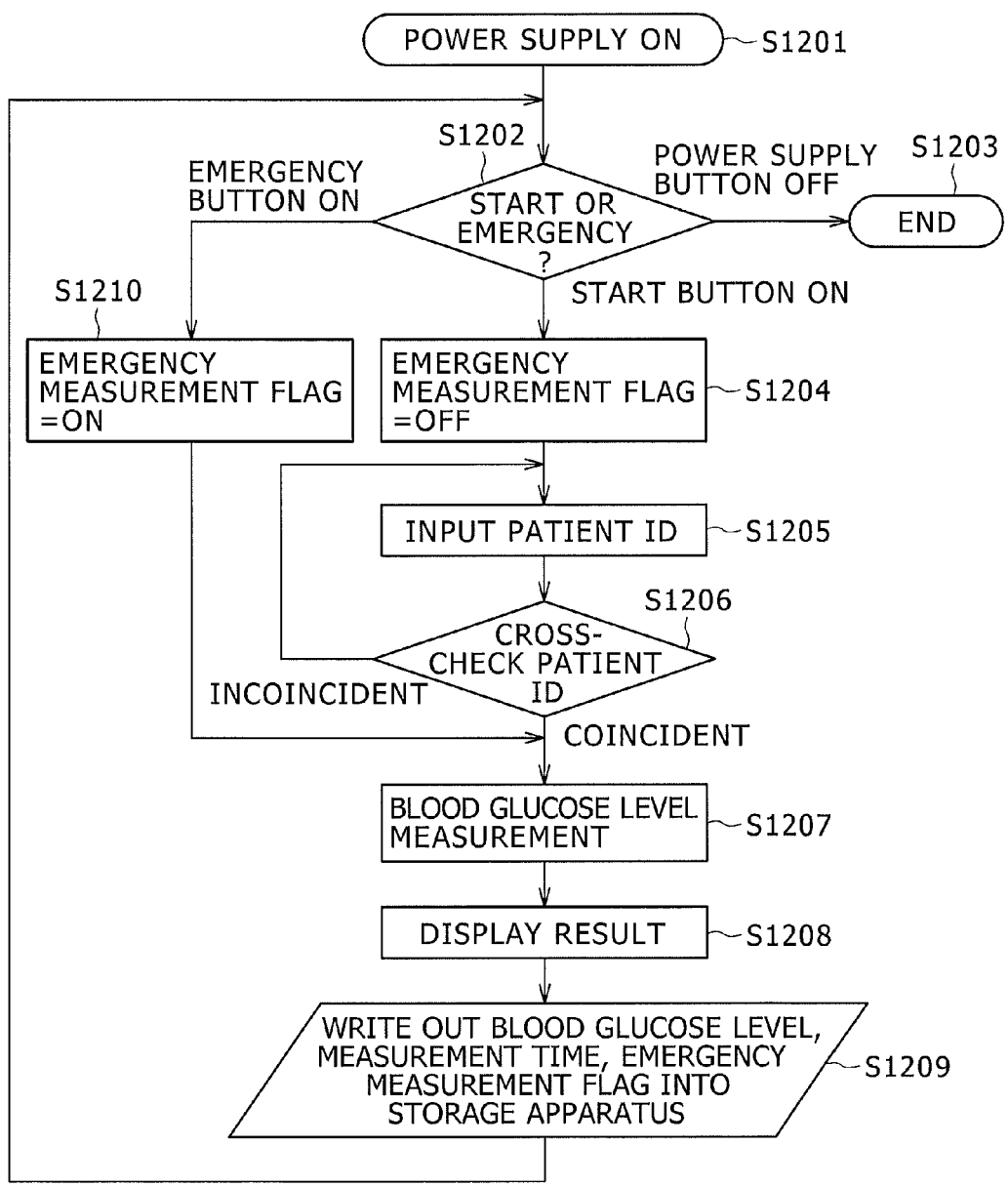
FIG. 12 is a flow chart illustrating an outline where flows of normal measurement and emergency measurement upon blood glucose measurement by the blood glucose meter are compared with each other.

Operation of the blood glucose meter 102 of the present invention can be summarized in the following manner. FIG. 12 is a flow chart of general operation of the blood glucose meter 102. If the power supply button 204 is depressed (S1201), then the blood glucose meter 102 is placed into a state in which it waits depression of the start button 205 or the emergency button 206 (S1202). Also it is possible to use a menu screen image displayed on the LCD unit 203 to urge the user to select the start button or the emergency button. Or, if nothing is carried out, then the normal measurement mode may be entered such that the emergency button 206 is used as an interrupt key to the CPU 602.

After the power supply button 204 is depressed to turn on the power supply to the blood glucose meter 102 (S1201), if the start button 205 is depressed (S1202), then the emergency measurement flag is changed to an off state (S1204), and processing of the blood glucose measurement system in a normal state is carried out and identification of a patient whose blood glucose level is to be measured is carried out. As described hereinabove, the patient ID applied to the patient is inputted, for example, by the barcode reading apparatus (S1205), and cross-checking with information for identifying patients stored in the storage unit is carried out (S1206). If the inputted patient ID exists in the patient list, then the blood glucose level of the patient is measured by the blood glucose level measuring unit (S1207). If the inputted patient ID does not exist in the patient list, then an alarm is displayed on the display unit and inputting of a new patient ID is waited.

If a blood glucose level is measured, then a result of the measurement is displayed on the display unit (S1208), and the blood glucose level and the time at which the blood glucose level is obtained are stored in an associated relationship with such information as the patient ID or the emergency measurement flag into the storage unit (S1209). Further, if the start button is depressed, then processing of the blood glucose measuring system regarding a next patient is carried out, and also it is possible to carry out blood glucose measurement repetitively.

Now, operation in the emergency measurement mode is described. After the LCD unit 203 is depressed to place the power supply to the blood glucose meter 102 into an ON state (S1201), by carrying out an operation for starting emergency measurement such as depression of the emergency measurement button at S1202, operation in the emergency measurement mode is started. In the emergency measurement mode, after the emergency measurement flag is placed into an ON state (S1210), identification of a patient which is carried out in a normal state is not carried out, but the blood glucose level is measured immediately by the blood glucose level measuring unit (S1207). After a blood glucose level is measured, a result of the measurement is displayed on the display unit (S1208), and the blood glucose level, the time at which the blood glucose level is obtained, the emergency measurement flag and so forth are stored into the storage unit (S1209). Here, if the start button is depressed, then it is also possible to carry out a process in a normal state of the blood glucose measuring system. If the power supply button 204 is depressed at S1202, then the power supply is turned OFF (S1203).

Figure 13:
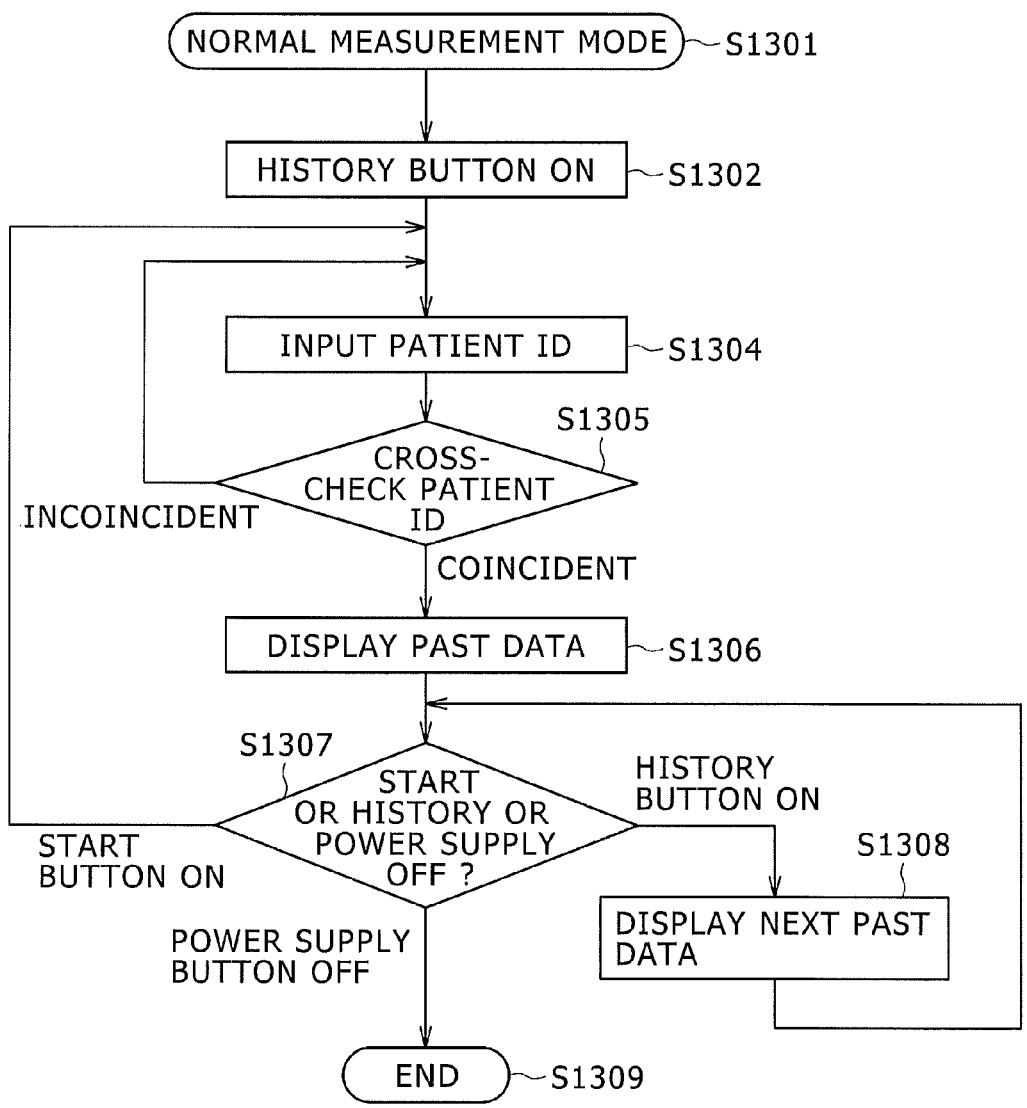
FIG. 13 is a flow chart illustrating a flow of browsing of a history in the normal measurement mode of the blood glucose meter.

Operation of browsing of a history in the normal measurement mode is described with reference to FIG. 13. After the power supply button 204 is depressed to place the power supply to the blood glucose meter 102 into an ON state (S1201), if the start button 205 is depressed, then the emergency measurement flag is placed into an off state (S1204) and a process of the blood glucose measuring system in an normal state is carried out. If the history button 207 is depressed (S1302) in this normal measurement mode (S1301), then identification of a patient whose history is to be displayed is carried out. As described hereinabove, the patient ID applied to the patient is inputted, for example, by the barcode reading apparatus (S1304) and cross-checking with information for identifying patients recorded in the patient data table 112 is carried out (S1305). If the inputted patient ID exists in the patient list, then the measurement data table 118 is referred to and the data with regard to which the time at which the blood glucose level of the inputted patient ID is newest is displayed on the LCD unit 203 (S1306). If the inputted patient ID does not exist in the patient list, then an alarm is displayed on the display unit and inputting of a new patient ID is waited. If the history button 207 is depressed at S1307, then the second newest data of the same patient is displayed similarly (S1308). If the start button 205 is depressed at S1307, then a state in which inputting of a new patient ID is waited is entered. If the power supply button 204 is depressed at S1307, then the power supply is placed into an OFF state (S1309).

Figure 14:
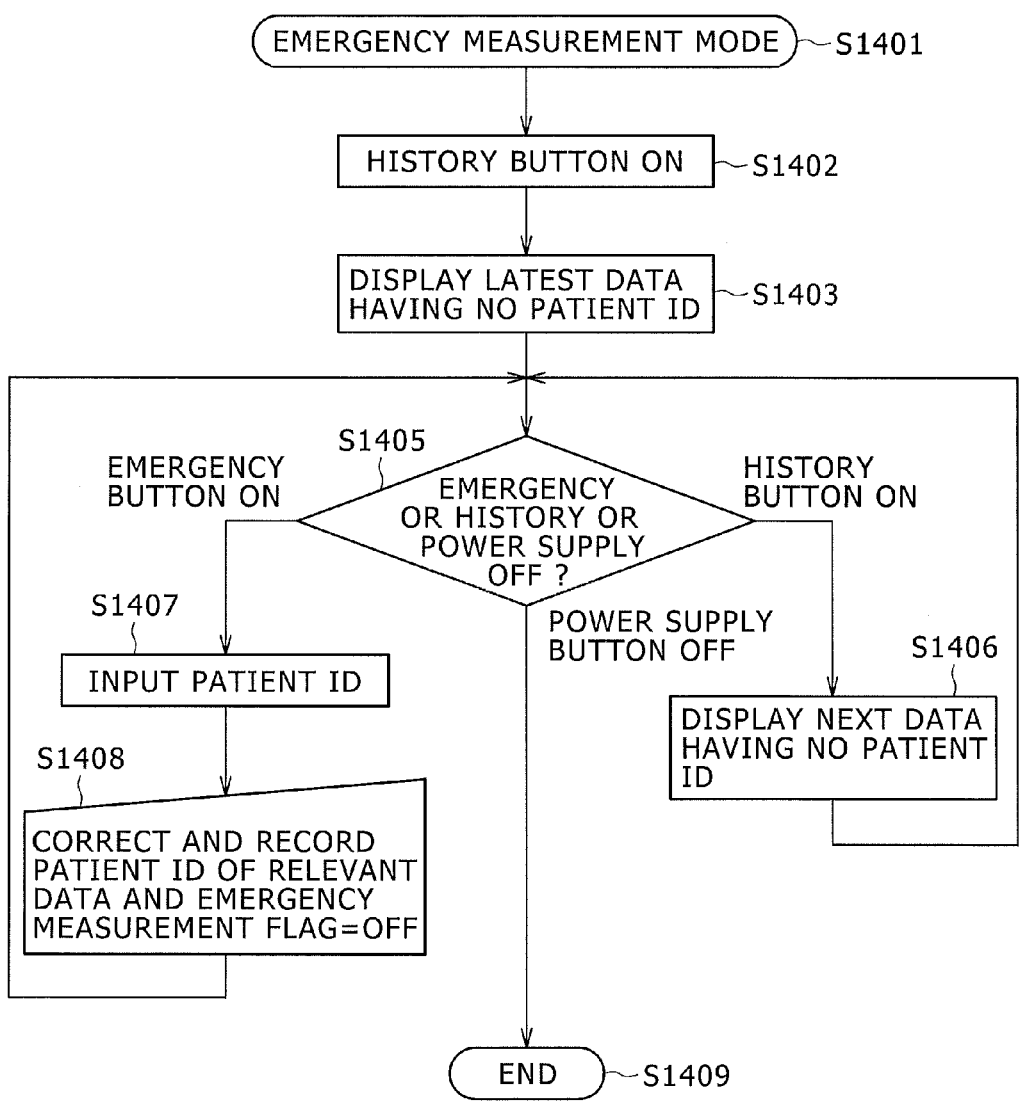
FIG. 14 is a flow chart illustrating a flow of association between browsing of a history and a patient ID in the emergency measurement mode of the blood glucose meter.

A process for browsing a result measured in the emergency measurement mode and associating information such as a patient ID later is described with reference to FIG. 14. If an operation for starting emergency measurement such as to depress the emergency measurement button at S1202 is carried out after the power supply button 204 is depressed to place the power supply to the blood glucose meter 102 into an ON state (S1201), then operation in the emergency measurement mode is started. If the history button 207 is depressed (S1402) in this emergency measurement mode (S1401), then the measurement data table 118 is searched and the data with regard to which the time at which a blood glucose level is obtained is newest from among data which do not have any patient ID is displayed on the LCD unit 203 (S1403). If the history button 207 is depressed at S1405, then the second newest data having no patient ID is displayed similarly (S1406). If the emergency button 206 is depressed at step S1405, then identification of a patient with which the displayed blood glucose level is to be associated is carried out. As described hereinabove, the patient ID applied to the patient is inputted, for example, by the barcode reading apparatus (S1407), and the patient ID inputted to the measurement data table 118 with regard to the displayed blood glucose level data are overwritten and the emergency measurement flag is placed into an off state (S1408). If the power supply button 204 is depressed at S1405, then the power supply is placed into an OFF state (S1409).

In the present embodiment, the blood glucose level measuring system includes a blood glucose level measuring apparatus and a measurement data management apparatus. A blood glucose level measuring apparatus includes identification means for acquiring patient identification information for identifying a patient, blood glucose level measuring means for measuring a blood glucose level of the patient, time counting means for obtaining information of date/time at which a blood glucose level is obtained by the blood glucose level measuring means, display means for displaying the patient identification information of the patient, the blood glucose level of the patient and the information of date/time at which the blood glucose level is obtained, a patient data table adapted to store the patient identification information, control means having a normal measurement mode in which the patient identification information acquired by the identification means and the patient data table are cross-checked with each other and then, if the patient identification information is found from within the patient data table, measurement of the blood glucose level by the blood glucose level measuring means is permitted but, if the patient identification information is not found from within the patient data table, measurement of the blood glucose level is inhibited and an emergency measurement mode in which carrying out of measurement of the blood glucose level is permitted without acquiring the patient identification information by the identification means, changing means for changing the measurement mode from the normal measurement mode to the emergency measurement mode, and a measurement data table in which, after the blood glucose level is obtained, in the normal measurement mode, the blood glucose level and the information of date/time at which the blood glucose level is obtained are recorded in an associated relationship with the patient identification information but, in the emergency measurement mode, the blood glucose level and the information of date/time at which the blood glucose level is obtained are recorded in an associated relationship with mode information which indicates the emergency measurement mode, under the control of the control means.

With the blood glucose level measuring apparatus, whereas rapid and reliable normal measurement is carried out, also emergency can be coped with relatively immediately.

The detailed description above describes features and aspects of embodiments of a blood glucose level measuring apparatus and a measurement data management apparatus. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A blood glucose level measuring apparatus comprising:
   identification means for acquiring patient identification information identifying a patient;
   blood glucose level measuring means for measuring blood glucose level of the patient;
   date/time counting means for obtaining date/time information identifying the date and time at which the blood glucose level is obtained by the blood glucose level measuring means;
   a display configured to display the patient identification information of the patient acquired by the identification means, the blood glucose level of the patient measured by the blood glucose level measuring means, and the date and time information obtained by the date/time counting means indicating the date and time at which the blood glucose level is obtained;
   a patient data table configured to store the patient identification information;
   control means for effecting control during: a normal measurement mode to cross-check the patient identification information acquired by the identification means and the patient data table, and, if the patient identification information is found in the patient data table, to permit measurement of the blood glucose level by the blood glucose level measuring means, but if the patient identification information is not found in the patient data table, to inhibit measurement of the blood glucose level; and an emergency measurement mode to permit measurement of the blood glucose level without acquiring the patient identification information by the identification means;
   changing means for changing the measurement mode from the normal measurement mode to the emergency measurement mode; and
   a measurement data table in which, after the blood glucose level is obtained in the normal measurement mode, the blood glucose level and the date/time information identifying the date and time at which the blood glucose level is obtained are recorded in an associated relationship with the patient identification information but, in the emergency measurement mode, the blood glucose level and the date/time information are recorded in an associated relationship with mode information indicating the emergency measurement mode, under the control of the control means.

2. The blood glucose level measuring apparatus according to claim 1, further comprising notification means for issuing, where the present mode is the emergency measurement mode, a notification that the present mode is the emergency measurement mode or is not the normal measurement mode.

3. The blood glucose level measuring apparatus according to claim 1, further comprising communication means for determining, regarding each of the blood glucose levels recorded in the measurement data table, the patient identification information, the blood glucose level, the date/time information indicating the date and time at which the blood glucose level is obtained and mode information as one string of transmission data in which a non-recorded item is determined as blank information, and transmitting the transmission data of all of the blood glucose levels recorded in the measurement data table to an external apparatus.

4. The blood glucose level measuring apparatus according to claim 1, wherein the control means also effects control during a history mode so that:

in the normal measurement mode, the blood glucose level and the date/time information which are associated with the selected patient identification information are displayed on the display; but in the emergency measurement mode, the blood glucose level, the date/time information and the mode information are displayed on the display and, if the identification means acquires the patient identification information, the blood glucose level and the date/time information are recorded into the measurement data table in an associated relationship with the patient identification information.

5. A measurement data management apparatus for managing data of the blood glucose level measuring apparatus according to claim 1, comprising:

host communication means for communicating with the communication means;

a patient history table adapted to record the blood glucose level and the date/time information in an associated relationship with the patient identification information;

a temporary patient measurement file adapted to record one string of transmission data and wherein the patient identification information is blank information; and host control means for extracting the patient identification information from the one string of transmission data and cross-checking the extracted patient identification information and said patient history table with each other and then: recording, if the patient identification information is found in the patient history table, the blood glucose level and the date/time information at which the blood glucose level is obtained into the patient history table in an associated relationship with the patient identification information; but recording, if the patient identification information is not found in the patient history table, the blood glucose level and the information of date/time into the temporary patient measurement file.

6. A method of measuring blood glucose level in a patient in a normal measurement mode and in an emergency measurement mode, the method comprising:

if the normal measurement mode is selected: acquiring patient identification information identifying a patient whose blood glucose level is to be measured; cross-checking the acquired patient identification information with a patient data table to determine if the patient identification information is in the patient data table; permitting measurement of the blood glucose level of the patient if the patient identification information is in the patient data table, identifying the blood glucose level of the patient and also identifying the date and time at which the blood glucose level of the patient is measured in the normal measurement mode; and preventing measurement of the blood glucose level if the patient identification information is not in the patient data table;

changing from the normal measurement mode to the emergency measurement mode;

identifying the blood glucose level of the patient measured in the emergency measurement mode, and also identifying the date and time at which the blood glucose level of the patient is measured in the emergency measurement mode, without acquiring the patient identification information identifying the patient whose blood glucose level is measured in the emergency measurement mode;

displaying the measured blood glucose level of the patient, and the date and time at which the blood glucose level of the patient is measured;

recording in an associated relationship in a measurement data table during the normal measurement mode: the blood glucose level, the date and time at which the blood glucose level is measured, and the patient identification information; and recording in an associated relationship in the measurement data table during the emergency measurement mode: the blood glucose level, the date and time at which the blood glucose level is measured, and emergency mode information identifying the emergency measurement mode.

7. The method according to claim 6, further comprising issuing a notification when a current measurement mode is the emergency measurement mode or is not the normal measurement mode.

8. The method according to claim 6, further comprising transmitting plural strings of measurement data to an external apparatus, each string of measurement data including: the blood glucose level, the patient identification information, and the date/time information recorded in the measurement data table in the associated relationship; or the blood glucose level, the date/time information, and the measurement mode recorded in the measurement data table in the associated relationship.

9. A blood glucose level measuring apparatus comprising:

identification means for acquiring patient identification information identifying a patient whose blood glucose is to be measured;

blood glucose meter comprising a reagent which interacts with a blood sample to provide a measurement of the blood glucose level of the patient;

date/time counting means for obtaining date/time information identifying the date and time at which the patient's blood glucose level is measured by the blood glucose meter;

a patient data table configured to store the patient identification information;

a display on which is displayed the patient identification information of the patient acquired by the identification means, the blood glucose level of the patient measured by the blood glucose meter, and the date/time information obtained by the date/time counting means;

changing means for changing a measurement mode during which the patient's blood glucose level is measured from a normal measurement mode to an emergency measurement mode;

control means for: permitting the blood glucose meter to measure the blood glucose level of the patient during the emergency measurement mode without requiring the identification means to acquire patient identification information; for permitting the blood glucose meter to measure the blood glucose level of the patient during the normal measurement mode when the patient identification information is acquired by the identification means and matches patient identification information in the patient data table; and for preventing the blood glucose meter from measuring the blood glucose level of the patient during the normal measurement mode when the patient identification information is acquired by the identification means but does not match patient identification information in the patient data table; and a measurement data table to which is recorded in an associated relationship: the blood glucose level measured in the normal measurement mode together with the date/time information identifying the date and time at which the blood glucose level is measured in the normal measurement mode; and the blood glucose level measured in the emergency measurement mode together with the date/time information identifying the date and time at which the blood glucose level is measured in the emergency measurement mode and mode information indicating the emergency measurement mode.

10. The blood glucose level measuring apparatus according to claim 9, further comprising notification means for issuing, where the present mode is the emergency measurement mode, a notification that the present mode is the emergency measurement mode or is not the normal measurement mode.

11. The blood glucose level measuring apparatus according to claim 9, wherein the date/time counting means, the patient data table and the measurement data table are located inside the blood glucose meter.

12. The blood glucose level measuring apparatus according to claim 9, further comprising communication means for determining, regarding each of the blood glucose levels recorded in the measurement data table, the patient identification information, the blood glucose level, the date/time information indicating the date and time at which the blood glucose level is obtained and mode information as one string of transmission data in which a non-recorded item is determined as blank information, and transmitting the strings of the transmission data of all of the blood glucose levels recorded in the measurement data table to an external apparatus.

* * * * *